US011756128B2

(12) United States Patent
Bryant et al.

(10) Patent No.: US 11,756,128 B2
(45) Date of Patent: Sep. 12, 2023

(54) DISTRIBUTED LEDGER SYSTEM FOR MANAGING SMART VEHICLE DATA

(71) Applicant: STATE FARM MUTUAL AUTOMOBILE INSURANCE COMPANY, Bloomington, IL (US)

(72) Inventors: Ronny S. Bryant, Bloomington, IL (US); Stacie A. McCullough, Bloomington, IL (US); Mitchell J. Hill, Bloomington, IL (US); Jacob J. Alt, Downs, IL (US); Jaime Skaggs, Chenoa, IL (US); Shawn M. Call, Bloomington, IL (US); Eric Bellas, Bloomington, IL (US); Vicki King, Bloomington, IL (US); Melinda Teresa Magerkurth, Utica, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 28 days.

(21) Appl. No.: 17/177,825

(22) Filed: Feb. 17, 2021

(65) Prior Publication Data

US 2021/0174609 A1 Jun. 10, 2021

Related U.S. Application Data

(63) Continuation of application No. 15/870,350, filed on Jan. 12, 2018, now Pat. No. 11,037,377.
(Continued)

(51) Int. Cl.
 G06Q 40/08 (2012.01)
 G06Q 30/0601 (2023.01)
(Continued)

(52) U.S. Cl.
 CPC ............. *G06Q 40/08* (2013.01); *B60W 50/00* (2013.01); *G06F 16/27* (2019.01); *G06Q 10/10* (2013.01);
(Continued)

(58) Field of Classification Search
 CPC ............... G06Q 40/08; G06Q 20/0389; G06Q 30/0283; G06Q 30/0623; G16H 10/60;
(Continued)

(56) References Cited

U.S. PATENT DOCUMENTS 5,499,182 A    3/1996  Ousborne
8,085,166 B2  12/2011  Tamir et al.
(Continued)

FOREIGN PATENT DOCUMENTS

WO    WO-2009044226 A1 *  4/2009  ........... G06Q 20/045
WO    WO-2017098519 A1    6/2017
(Continued)

OTHER PUBLICATIONS

Mainelli et al: "Sharing ledgers for sharing economies: an exploration of mutual distributed ledgers (aka blockchain technology)", The Journal of Financial Perspectives: FinTech, EY Global Financial Services Institute, vol. 3—Issue 3, Winter 2015 (Year: 2015).
(Continued)

*Primary Examiner* — Scott C Anderson
(74) *Attorney, Agent, or Firm* — MARSHALL, GERSTEIN & BORUN LLP

(57) ABSTRACT

Systems and methods are disclosed with respect to using a distributed ledger, such as a blockchain, for managing smart vehicle data. The managed data may relate to a detected vehicle event, such as: a motion or position detected by a motion or position sensor as a GPS chip, an accelerometer, a compass, a speedometer, a gyroscope, etc.; braking detected by a braking sensor; turn input detected by a
(Continued)

steering wheel sensor; wheel position detected by a wheel sensor; engine temperature detected by a temperature gauge; oil temperature detected by a temperature gauge; a seatbelt status detected by a seatbelt and/or seat sensor; etc.

20 Claims, 14 Drawing Sheets

Related U.S. Application Data

(60) Provisional application No. 62/548,692, filed on Aug. 22, 2017, provisional application No. 62/548,731, filed on Aug. 22, 2017, provisional application No. 62/548,679, filed on Aug. 22, 2017, provisional application No. 62/548,741, filed on Aug. 22, 2017, provisional application No. 62/548,700, filed on Aug. 22, 2017, provisional application No. 62/548,682, filed on Aug. 22, 2017, provisional application No. 62/548,748, filed on Aug. 22, 2017, provisional application No. 62/548,668, filed on Aug. 22, 2017, provisional application No. 62/545,262, filed on Aug. 14, 2017, provisional application No. 62/508,133, filed on May 18, 2017, provisional application No. 62/500,049, filed on May 2, 2017, provisional application No. 62/500,326, filed on May 2, 2017.

(51) Int. Cl.
| | |
|---|---|
| *H04W 4/40* | (2018.01) |
| *G06F 16/27* | (2019.01) |
| *B60W 50/00* | (2006.01) |
| *G07C 5/00* | (2006.01) |
| *G07C 5/08* | (2006.01) |
| *H04L 67/1061* | (2022.01) |
| *H04L 67/12* | (2022.01) |
| *G06Q 10/10* | (2023.01) |
| *G06Q 20/38* | (2012.01) |
| *H04L 9/06* | (2006.01) |
| *H04L 12/28* | (2006.01) |
| *H04L 9/32* | (2006.01) |
| *G06Q 30/0283* | (2023.01) |
| *G16H 10/60* | (2018.01) |
| *G06F 16/903* | (2019.01) |
| *H04L 9/00* | (2022.01) |

(52) U.S. Cl.
CPC ....... *G06Q 20/389* (2013.01); *G06Q 30/0283* (2013.01); *G06Q 30/0623* (2013.01); *G07C 5/008* (2013.01); *G07C 5/0808* (2013.01); *G16H 10/60* (2018.01); *H04L 9/0643* (2013.01); *H04L 9/32* (2013.01); *H04L 12/2803* (2013.01); *H04L 67/1061* (2013.01); *H04L 67/12* (2013.01); *H04W 4/40* (2018.02); *B60W 2756/10* (2020.02); *G06F 16/903* (2019.01); *H04L 9/50* (2022.05); *H04L 2012/2847* (2013.01)

(58) Field of Classification Search
CPC ....... G06F 16/27; G07C 5/008; G07C 5/0808; H04W 4/40; B60W 50/00
See application file for complete search history.

(56) References Cited

U.S. PATENT DOCUMENTS

| | | |
|---|---|---|
| 8,106,769 B1 | 1/2012 | Maroney et al. |
| 8,374,957 B1 | 2/2013 | Garcia et al. |
| 8,756,085 B1 | 6/2014 | Plummer et al. |
| 9,141,582 B1 | 9/2015 | Brinkmann et al. |
| 9,298,806 B1 * | 3/2016 | Vessenes .............. G06Q 20/065 |
| 9,311,271 B2 | 4/2016 | Wright |
| 9,633,487 B2 | 4/2017 | Wright |
| 9,646,029 B1 | 5/2017 | Baird, III |
| 9,811,863 B1 | 11/2017 | Marinescu et al. |
| 9,824,453 B1 * | 11/2017 | Collins ..................... G06T 7/60 |
| 9,855,785 B1 * | 1/2018 | Nagelberg ........ G06K 19/06028 |
| 9,998,286 B1 | 6/2018 | Ramathal et al. |
| 10,192,369 B2 | 1/2019 | Wright |
| 10,198,879 B2 | 2/2019 | Wright |
| 10,269,009 B1 | 4/2019 | Winklevoss et al. |
| 10,340,038 B2 | 7/2019 | Witchey |
| 10,341,309 B1 | 7/2019 | Ramirez et al. |
| 10,366,204 B2 | 7/2019 | Tanner, Jr. et al. |
| 10,430,883 B1 | 10/2019 | Bischoff et al. |
| 10,430,889 B1 | 10/2019 | Ismaili et al. |
| 10,454,878 B2 | 10/2019 | Khan et al. |
| 10,510,120 B1 | 12/2019 | Roll |
| 10,521,780 B1 | 12/2019 | Hopkins, III et al. |
| 10,554,649 B1 | 2/2020 | Fields et al. |
| 10,586,062 B1 | 3/2020 | Rangan et al. |
| 10,606,669 B2 | 3/2020 | Jacobs et al. |
| 10,679,221 B1 | 6/2020 | Rutley et al. |
| 10,685,009 B1 | 6/2020 | Rutley et al. |
| 10,713,727 B1 | 7/2020 | Floyd et al. |
| 10,726,493 B1 | 7/2020 | Kyne et al. |
| 10,733,616 B1 | 8/2020 | Rutley et al. |
| 10,796,371 B1 | 10/2020 | Floyd et al. |
| 10,796,393 B2 | 10/2020 | Messerges et al. |
| 10,805,085 B1 | 10/2020 | Liang |
| 10,832,337 B1 | 11/2020 | Floyd et al. |
| 10,832,338 B1 | 11/2020 | Floyd et al. |
| 10,833,843 B1 | 11/2020 | Vijayvergia et al. |
| 10,872,381 B1 | 12/2020 | Leise et al. |
| 10,878,512 B1 | 12/2020 | Al-Zoubi et al. |
| 10,891,694 B1 | 1/2021 | Leise et al. |
| 10,971,251 B1 | 4/2021 | Giobbi et al. |
| 2002/0022976 A1 | 2/2002 | Hartigan |
| 2005/0276401 A1 | 12/2005 | Madill et al. |
| 2006/0212195 A1 | 9/2006 | Veith et al. |
| 2006/0253351 A1 | 11/2006 | Keaney |
| 2006/0282342 A1 | 12/2006 | Chapman |
| 2007/0185743 A1 | 8/2007 | Jinks |
| 2008/0255722 A1 | 10/2008 | McClellan et al. |
| 2009/0024419 A1 | 1/2009 | McClellan et al. |
| 2009/0327006 A1 | 12/2009 | Hansan et al. |
| 2010/0223078 A1 | 9/2010 | Willis et al. |
| 2011/0090075 A1 | 4/2011 | Armitage et al. |
| 2011/0106370 A1 | 5/2011 | Duddle et al. |
| 2011/0161116 A1 | 6/2011 | Peak et al. |
| 2011/0213628 A1 | 9/2011 | Peak et al. |
| 2011/0320492 A1 | 12/2011 | Inghelbrecht |
| 2012/0029945 A1 | 2/2012 | Altieri et al. |
| 2012/0053965 A1 | 3/2012 | Hellman et al. |
| 2012/0066007 A1 | 3/2012 | Ferrick et al. |
| 2014/0063232 A1 | 3/2014 | Fairfield et al. |
| 2014/0129261 A1 | 5/2014 | Bothwell et al. |
| 2014/0278582 A1 * | 9/2014 | Shambach .............. G06Q 40/08 |
| | | 705/4 |
| 2014/0278585 A1 | 9/2014 | Zerbib |
| 2014/0368601 A1 | 12/2014 | deCharms |
| 2015/0006205 A1 | 1/2015 | Chase et al. |
| 2015/0170112 A1 | 6/2015 | DeCastro |
| 2015/0310476 A1 | 10/2015 | Gadwa |
| 2015/0332283 A1 | 11/2015 | Witchey |
| 2015/0356686 A1 | 12/2015 | Cook et al. |
| 2016/0027121 A1 | 1/2016 | Lucia et al. |
| 2016/0048923 A1 | 2/2016 | Maher et al. |
| 2016/0171619 A1 | 6/2016 | Besman et al. |
| 2016/0217532 A1 | 7/2016 | Slavin |
| 2016/0224949 A1 | 8/2016 | Thomas et al. |
| 2016/0260169 A1 | 9/2016 | Arnold et al. |
| 2016/0358135 A1 | 12/2016 | Liao et al. |
| 2016/0378943 A1 | 12/2016 | Vallee |
| 2017/0034197 A1 | 2/2017 | Daniel et al. |
| 2017/0046526 A1 | 2/2017 | Chan et al. |
| 2017/0046651 A1 | 2/2017 | Lin et al. |
| 2017/0046792 A1 | 2/2017 | Haldenby et al. |

(56) References Cited

U.S. PATENT DOCUMENTS

| | | | |
|---|---|---|---|
| 2017/0048216 A1* | 2/2017 | Chow | G06Q 40/08 |
| 2017/0053461 A1 | 2/2017 | Pal et al. | |
| 2017/0069034 A1 | 3/2017 | Luciani | |
| 2017/0075941 A1 | 3/2017 | Finlow-Bates | |
| 2017/0091397 A1 | 3/2017 | Shah | |
| 2017/0124556 A1 | 5/2017 | Seger, II | |
| 2017/0124658 A1* | 5/2017 | Gordon | G06Q 40/08 |
| 2017/0161439 A1 | 6/2017 | Raduchel et al. | |
| 2017/0177898 A1 | 6/2017 | Dillenberger | |
| 2017/0220998 A1 | 8/2017 | Horn et al. | |
| 2017/0300627 A1 | 10/2017 | Giordano et al. | |
| 2017/0372431 A1 | 12/2017 | Perl et al. | |
| 2018/0018723 A1 | 1/2018 | Nagla et al. | |
| 2018/0039667 A1 | 2/2018 | Pierce et al. | |
| 2018/0040007 A1 | 2/2018 | Lane et al. | |
| 2018/0046992 A1 | 2/2018 | Hanrahan et al. | |
| 2018/0101848 A1 | 4/2018 | Castagna et al. | |
| 2018/0165416 A1 | 6/2018 | Saxena et al. | |
| 2018/0183600 A1 | 6/2018 | Davis | |
| 2018/0205546 A1 | 7/2018 | Haque et al. | |
| 2018/0218455 A1 | 8/2018 | Kolb et al. | |
| 2018/0225660 A1 | 8/2018 | Chapman et al. | |
| 2018/0247376 A1 | 8/2018 | Sharma et al. | |
| 2018/0267539 A1 | 9/2018 | Shih | |
| 2018/0276054 A1 | 9/2018 | Furuichi et al. | |
| 2018/0287915 A1* | 10/2018 | Smith | H04L 51/23 |
| 2018/0308072 A1 | 10/2018 | Smith et al. | |
| 2019/0019186 A1 | 1/2019 | Falah et al. | |
| 2019/0057454 A1 | 2/2019 | Komenda et al. | |
| 2019/0080392 A1 | 3/2019 | Youb et al. | |
| 2019/0123889 A1 | 4/2019 | Schmidt-Karaca | |
| 2019/0197620 A1 | 6/2019 | Jayaram et al. | |
| 2019/0279227 A1 | 9/2019 | Chantz | |
| 2019/0287140 A1 | 9/2019 | Arora et al. | |
| 2019/0303931 A1 | 10/2019 | Valencia | |
| 2019/0318816 A1 | 10/2019 | Witchey | |
| 2019/0354966 A1 | 11/2019 | Himura et al. | |
| 2019/0392437 A1 | 12/2019 | Castagna et al. | |
| 2019/0392438 A1 | 12/2019 | Rice | |
| 2020/0020037 A1 | 1/2020 | Idrobo | |
| 2020/0058071 A1 | 2/2020 | Yang | |
| 2020/0065763 A1 | 2/2020 | Rosinzonsky et al. | |
| 2020/0177373 A1 | 6/2020 | Komandur et al. | |
| 2020/0226677 A1 | 7/2020 | Dhawan et al. | |
| 2020/0250753 A1 | 8/2020 | Blount | |
| 2020/0272966 A1 | 8/2020 | Kirkegaard | |
| 2020/0279328 A1 | 9/2020 | Zhiri et al. | |
| 2020/0341971 A1 | 10/2020 | Krishnaswamy et al. | |
| 2020/0394321 A1 | 12/2020 | Ramos et al. | |
| 2020/0394322 A1 | 12/2020 | Ramos et al. | |
| 2020/0409937 A1 | 12/2020 | Wang et al. | |
| 2021/0065293 A1 | 3/2021 | Sigler et al. | |
| 2021/0090037 A1 | 3/2021 | Dowding | |
| 2021/0174442 A1 | 6/2021 | Trudeau et al. | |

FOREIGN PATENT DOCUMENTS

| | | |
|---|---|---|
| WO | WO-2017136879 A1 | 8/2017 |
| WO | WO-2017145009 A1 | 8/2017 |
| WO | WO-2020/169129 A2 | 8/2020 |
| WO | WO-2021/046494 A1 | 3/2021 |

OTHER PUBLICATIONS

"Blockchain in the insurance sector," Web page <https://www.pwc.co.uk/financialservices/fintech/assets/blockchain-in-insurance.pdf>, 2 pages, dated Aug. 7, 2016 by the Internet Archive Wayback Machine; retrieved from the Internet Archive Wayback Machine <http://web.archive.org/web/*/https://www.pwc.co.uk/financial-services/fintech/assets/blockchain-in-insurance.pdf> on Apr. 12, 2021.
Cointelegraph, "HashCoin Uses Emercoin Blockchain for Vehicle Registration and Tracking," Retrieved from the Internet at: <https://cointelegraph.com/news/hashcoin-uses-emercoin-blockchain-forvehicle-registration-and-tracking> dated Dec. 8, 2016.
Blockchain in the insurance sector. Retrieved from the internet at: <URL: https://www.pwc.co.uk (2016).
HashCoin Uses Emercoin Blockchain for Vehicle Registration and Tracking. Retrieved from the internet at: <URL: https://cointelegraph.com/news/hashcoin-uses-emercoin-blockchain-for-vehicle-registration-and-tracking (2018).
U.S. Appl. No. 14/871,401, filed Sep. 30, 2015, "System and Method for Obtaining and/or Maintaining Insurance Coverage".
U.S. Appl. No. 15/457,705, filed Mar. 13, 2017, "System and Method for Obtaining and/or Maintaining Insurance Coverage".
U.S. Appl. No. 15/600,968, filed May 22, 2017, "Systems and Methods for Blockchain Validation of Consumer Identity and Authority".
U.S. Appl. No. 15/604,178, filed May 24, 2017, "Systems and Methods for Generating a Blockchain-based Consumer Profile".
U.S. Appl. No. 15/624,278, filed Jun. 15, 2017, "Systems and Methods for Building and Utilizing an Autonomous Vehicle-Related Event Blockchain".
U.S. Appl. No. 15/624,287, filed Jun. 15, 2017, "Systems and Methods for Maintaining a Distributed Ledger Pertaining to Smart Contracts".
U.S. Appl. No. 15/624,292, filed Jun. 15, 2017, "Systems and Methods for Building, Utilizing, and/or Maintaining an Autonomous Vehicle-Related Event Distributed Ledger or Blockchain".
U.S. Appl. No. 15/624,307, filed Jun. 15, 2017, "Systems and Methods for Maintaining a Distributed Ledger of Transactions Pertaining to an Autonomous Vehicle".
U.S. Appl. No. 15/624,334, filed Jun. 15, 2017, "Systems and Methods for Maintaining a Distributed Ledger of Transactions Pertaining to One or More Smart Contracts".
U.S. Appl. No. 15/624,341, filed Jun. 15, 2017, "Systems and Methods for Maintaining a Distributed Ledger Pertaining to Autonomous Vehicles".
U.S. Appl. No. 15/704,339, filed Sep. 14, 2017, "Systems and Methods for Obtaining and/or Maintaining Usage-Based Insurance".
U.S. Appl. No. 15/704,350, filed Sep. 14, 2017, "Systems and Methods for Obtaining and/or Maintaining Insurance for Autonomous Vehicles".
U.S. Appl. No. 15/704,363, filed Sep. 14, 2017, "Systems and Methods for Determining and Providing Insurance to Affinitiy Groups".
U.S. Appl. No. 15/704,632, filed Sep. 14, 2017, Systems and Methods for Obtaining and/or Securing Insurance for Affinity Groups.
U.S. Appl. No. 15/863,208, filed Jan. 5, 2018, "Providing Temporary Insurance Coverage Using Temorary Risk Data".
U.S. Appl. No. 15/863,243, filed Jan. 5, 2018, "Providing Temporary Insurance Coverage Using Temorary Risk Data".
U.S. Appl. No. 15/863,284, filed Jan. 5, 2018, "Providing Temporary Insurance Coverage Using Temorary Risk Data".
U.S. Appl. No. 15/863,327, filed Jan. 5, 2018, Providing Temporary Insurance Coverage Using Temorary Risk Data.
U.S. Appl. No. 15/869,685, filed Jan. 12, 2018, "Risk Mitigation for Affinity Groupings".
U.S. Appl. No. 15/869,752, filed Jan. 12, 2018, "Blockchain Systems and Methods for Providing Insurance Coverage to Affinity Groups".
U.S. Appl. No. 15/870,271, filed Jan. 12, 2018, "Distributed Ledger System for Managing Loss Histories for Properties".
U.S. Appl. No. 15/870,282, filed Jan. 12, 2018, "Distributed Ledger System for Managing Vehicle Sensor Data Utilized to Develop Collision Profiles".
U.S. Appl. No. 15/870,292, filed Jan. 12, 2018, "Distributed Ledger System for Use With Vehicle Sensor Data and Usage Based Systems".
U.S. Appl. No. 15/870,298, filed Jan. 12, 2018, "Distributed Ledger System for Managing Medical Records".
U.S. Appl. No. 15/870,332, filed Jan. 12, 2018, "Distributed Ledger System for Insurance Record Management Systems".

(56) References Cited

OTHER PUBLICATIONS

U.S. Appl. No. 15/870,343, filed Jan. 12, 2018, "Distributed Ledger System for Managing Smart Home Data".
U.S. Appl. No. 15/870,350, filed Jan. 12, 2018, "Distributed Ledger System for Managing Smart Vehicle Data".
U.S. Appl. No. 15/870,357, filed Jan. 12, 2018, "Distributed Ledger System for Claim Payouts".
U.S. Appl. No. 15/870,364, filed Jan. 12, 2018, "Distributed Ledger System for Carrier Discovery".
U.S. Appl. No. 15/870,371, filed Jan. 12, 2018, "Distributed Ledger System for Managing Loss Histories for Individuals".
U.S. Appl. No. 15/877,982, filed Jan. 23, 2018, "Blockchain Banking Identity Authentication".
U.S. Appl. No. 15/878,007, filed Jan. 23, 2018, "Blockchain Based Account Funding and Distribution".
U.S. Appl. No. 15/878,028, filed Jan. 23, 2018, "Blockchain Based Card Activation".
U.S. Appl. No. 15/878,046, filed Jan. 23, 2018, "Blockchain Based Passing Registry Actions".
U.S. Appl. No. 15/878,067, filed Jan. 23, 2018, "Blockchain Based Asset Access".
U.S. Appl. No. 15/878,082, filed Jan. 23, 2018, "Blockchain Based Lien Perfection".
U.S. Appl. No. 15/878,106, filed Jan. 23, 2018, "Blockchain Based Settlement Processes".
U.S. Appl. No. 15/878,125, filed Jan. 23, 2018, "Blockchain Based Contractor Ratings".
U.S. Appl. No. 15/878,140, filed Jan. 23, 2018, "Blockchain Based Customer Records".
U.S. Appl. No. 15/878,154, filed Jan. 23, 2018, "Blockchain Based Associate Information and Licensing".
U.S. Patent Application No. 62/508,133, filed May 18, 2017, "Distributed Ledger System for Managing Smart Home Data, Vehicle Data, Insurance Claim Payouts, and/or Insurance Carrier Discovery".
U.S. Appl. No. 62/425,684, filed Nov. 23, 2016, "Systems and Methods for Maintaining a Distributed Ledger Governing Autonomous Vehicle Transactions".
U.S. Appl. No. 62/428,223, filed Nov. 30, 2016, "Systems and Methods for Maintaining a Distributed Ledger Governing Autonomous Vehicle Transactions".
U.S. Appl. No. 62/434,215, filed Dec. 14, 2016, "Systems and Methods for Maintaining a Distributed Ledger Governing Autonomous Vehicle Transactions".
U.S. Appl. No. 62/447,240, filed Jan. 17, 2017, "Providing Temporary Insurance Coverage Using Temorary Risk Data".
U.S. Appl. No. 62/449,405, filed Jan. 23, 2017, Providing Temporary Insurance Coverage Using Temorary Risk Data.
U.S. Appl. No. 62/450,349, filed Jan. 25, 2017, "Systems and Methods for Securely Incorporating Blockchain Technology".
U.S. Appl. No. 62/450,441, filed Jan. 25, 2017, "Using Blockchain for Banking, Asset, and Identify Services".
U.S. Appl. No. 62/457,430, filed Feb. 10, 2017, "Systems and Methods for Maintaining a Distributed Ledger Governing Autonomous Vehicle Transactions".
U.S. Appl. No. 62/466,917, filed Mar. 3, 2017, "Blockchain Vin Registry".
U.S. Appl. No. 62/468,092, filed Mar. 7, 2017, "Blockchain Vin Registry".
U.S. Appl. No. 62/469,070, filed Mar. 9, 2017, "Using Blockchain for Banking, Asset, and Identify Services".
U.S. Appl. No. 62/471,224, filed Mar. 17, 2017, "System and Method for Obtaining and/or Maintaining Insurance Coverage".
U.S. Appl. No. 62/474,900, filed Mar. 22, 2017, "Providing Temporary Insurance Coverage Using Temorary Risk Data".
U.S. Appl. No. 62/481,888, filed Apr. 5, 2017, "Using a Blockchain for Vehicle Lifecycle Processes".
U.S. Appl. No. 62/482,792, filed Apr. 7, 2017, "Using a Blockchain for Vehicle Lifecycle Processes".
U.S. Appl. No. 62/485,725, filed Apr. 14, 2017, "System and Method for Obtaining and/or Maintaining Insurance Coverage".
U.S. Appl. No. 62/500,049, filed May 2, 2017, "Distributed Ledger System".
U.S. Appl. No. 62/500,326, filed May 2, 2017, "Distributed Ledger System".
U.S. Appl. No. 62/501,621, filed May 4, 2017, "Using a Blockchain for Vehicle Lifecycle Processes".
U.S. Appl. No. 62/503,184, filed May 8, 2017, "System and Method for Obtaining and/or Maintaining Insurance Coverage".
U.S. Appl. No. 62/504,328, filed May 10, 2017, "Method of Approving Dynamic Mortgage Application".
U.S. Appl. No. 62/509,479, filed May 22, 2017, "Using a Blockchain for Vehicle Lifecycle Processes".
U.S. Appl. No. 62/509,557, filed May 22, 2017, "Providing Temporary Insurance Coverage Using Temorary Risk Data".
U.S. Appl. No. 62/510,664, filed May 24, 2017, "Blockchain Subrogation Payments".
U.S. Appl. No. 62/514,470, filed Jun. 2, 2017, "System and Method of Utilizing Blockchain Technology to Approve and Update Dynamic Mortgage Applications".
U.S. Appl. No. 62/515,923, filed Jun. 6, 2017, "Providing Temporary Insurance Coverage Using Temorary Risk Data".
U.S. Appl. No. 62/520,376, filed Jun. 15, 2017, "Blockchain Based Banking Identity Authentication".
U.S. Appl. No. 62/520,401, filed Jun. 15, 2017, "Blockchain Based Account Funing and Distribution".
U.S. Appl. No. 62/520,648, filed Jun. 16, 2017, "Blockchain Based Card Activation".
U.S. Appl. No. 62/520,708, filed Jun. 16, 2017, "Blockchain Based Passing Registry Actions".
U.S. Appl. No. 62/521,784, filed Jan. 25, 2018, "Technology for Building and Managing Data Models".
U.S. Appl. No. 62/523,523, filed Jun. 22, 2017, "Blockchain Based Asset Access".
U.S. Appl. No. 62/528,791, filed Jul. 5, 2017, "Blockchain Based Lien Perfection".
U.S. Appl. No. 62/528,806, filed Jul. 5, 2017, "Blockchain Based Settlement Processes".
U.S. Appl. No. 62/532,072, filed Jul. 13, 2017, "Blockchain Based Contractor Ratings".
U.S. Appl. No. 62/532,089, filed Jul. 13, 2017, "Blockchain Based Customer Records".
U.S. Appl. No. 62/532,102, filed Jul. 13, 2017, "Blockchain Based Associate Information and Licensing".
U.S. Appl. No. 62/535,018, filed Jul. 20, 2017, "System and Method of Approving and Updating Dynamic Mortgage Applications".
U.S. Appl. No. 62/536,600, filed Jul. 25, 2017, "Systems and Methods for Controlled Access to Blockchain Data".
U.S. Appl. No. 62/536,672, filed Jul. 25, 2017, "Systems and Methods for Controlled Access to Policy Data on Blockchain".
U.S. Appl. No. 62/536,683, filed Jul. 25, 2017, "Systems and Methods for Controlled Access to Audit Data on Blockchain".
U.S. Appl. No. 62/536,698, filed Jul. 25, 2017, "Systems and Methods for Securely Filing Documents via Blockchain".
U.S. Appl. No. 62/536,704, filed Jul. 25, 2017, "Systems and Methods for Verifying Agent Sales Data via Blockchain".
U.S. Appl. No. 62/536,709, filed Jul. 25, 2017, "Systems and Methods for Fund Transfers via Blockchain".
U.S. Appl. No. 62/536,715, filed Jul. 25, 2017, "Systems and Methods for Anti-Money Laundering Compliance via Blockchain".
U.S. Appl. No. 62/536,716, filed Jul. 25, 2017, "Systems and Methods for Industry Reporting via Blockchain".
U.S. Appl. No. 62/536,735, filed Jul. 25, 2017, "Sytems and Methods for Insurable Interest Validation via Blockchain".
U.S. Appl. No. 62/536,754, filed Jul. 25, 2017, "Sytems and Methods for Blockchain-Based Payments".
U.S. Appl. No. 62/537,084, filed Jul. 26, 2017, "System and Methods for Maintaining Transferability of Title via Blockchain".
U.S. Appl. No. 62/540,299, filed Aug. 2, 2017, "Systems and Methods for Recall Compliance via Blockchain".
U.S. Appl. No. 62/541,363, filed Aug. 4, 2017, "Systems and Methods for Sensor Recalibration via Blockchain".

(56) References Cited

OTHER PUBLICATIONS

U.S. Appl. No. 62/541,386, filed Aug. 4, 2017, "Systems and Methods for Feature-Based via Blockchain".
U.S. Appl. No. 62/542,066, filed Aug. 7, 2017, "Systems and Methods for Total Loss Handling via Blockchain".
U.S. Appl. No. 62/542,081, filed Aug. 7, 2017, "Systems and Methods for Analyzing Vehicle Financing via Blockchain".
U.S. Appl. No. 62/542,456, filed Aug. 8, 2017, "Systems and Methods for Usage Based Insurance via Blockchain".
U.S. Appl. No. 62/542,477, filed Aug. 8, 2017, "Systems and Methods for Estimating Vehicle Value via Blockchain".
U.S. Appl. No. 62/542,496, filed Aug. 8, 2017, "Systems and Methods for Post-Collision Vehicle Routing via Blockchain".
U.S. Appl. No. 62/545,262, filed Aug. 14, 2017, "Distributed Ledger System for Managing Loss Histories".
U.S. Appl. No. 62/548,668, filed Aug. 22, 2017, "Distributed Ledger System for Managing Vehicle Sensor Data Utilized to Develop Collision Profiles".
U.S. Appl. No. 62/548,679, filed Aug. 22, 2017, "Distributed Ledger System for Use with Vehicle Sensor Data and Usage Based Systems".
U.S. Appl. No. 62/548,682, filed Aug. 22, 2017, "Distributed Ledger System for Manging Medical Records".
U.S. Appl. No. 62/548,692, filed Aug. 22, 2017, "Distributed Ledger System for Insurance Record Management Systems".
U.S. Appl. No. 62/548,700, filed Aug. 22, 2017, "Distributed Ledger System for Managing Smart Vehicle Data".
U.S. Appl. No. 62/548,731, filed Aug. 22, 2017, "Distributed Ledger System for Claim Payouts".
U.S. Appl. No. 62/548,741, filed Aug. 22, 2017, "Distributed Ledger System for Smart Home Data".
U.S. Appl. No. 62/548,748, filed Aug. 22, 2017, Distributed Ledger System for Carrier Discovery.
U.S. Appl. No. 62/550,131, filed Aug. 25, 2017, "Maintaining a Distributed Ledger for VIN Recordkeeping".
U.S. Appl. No. 62/550,140, filed Aug. 25, 2017, "Using a Distributed Ledger for Total Loss Management".
U.S. Appl. No. 62/550,172, filed Aug. 25, 2017, "Using a Distributed Ledger for Tracking VIN Recordkeeping".
U.S. Appl. No. 62/550,186, filed Aug. 25, 2017, "Smart Contracts for Vehicle Events".
U.S. Appl. No. 62/550,197, filed Aug. 25, 2017, "Using a Distributed Ledger for Tracking Vehicle Financial Events".
U.S. Appl. No. 62/550,224, filed Aug. 25, 2017, "Using a Distributed Ledger for the Auto Claims Process".
U.S. Appl. No. 62/550,245, filed Aug. 25, 2017, "Using a Distributed Ledger to Track a VIN Lifecycle".
U.S. Appl. No. 62/550,261, filed Aug. 25, 2017, "Using a Distributed Ledger for Proof of Insurance".
U.S. Appl. No. 62/551,618, filed Aug. 29, 2017, "Risk Mitigation for Affinity Groupings".
U.S. Appl. No. 62/554,907, filed Sep. 6, 2017, "Blockchain Based Claim Handling".
U.S. Appl. No. 62/555,014, filed Sep. 6, 2017, "Fault Determination of Blockchain Subrogation Claims".
U.S. Appl. No. 62/555,030, filed Sep. 6, 2017, "Using a Blockchain for the Subrogation Claim Process".
U.S. Appl. No. 62/555,177, filed Sep. 7, 2017, "Fault Determination of Blockchain Subrogation Claims".
U.S. Appl. No. 62/555,358, filed Sep. 7, 2017, "Using a Blockchain for the Subrogation Claim Process".
U.S. Appl. No. 62/563,818, filed Sep. 27, 2017, "Automated Section of a Vehicle".
U.S. Appl. No. 62/581,292, filed Nov. 3, 2017, "Approving and Updating Dynamic Mortgage Applications".
U.S. Appl. No. 62/581,323, filed Nov. 3, 2017, "Continuously Monitoring and Updating Mortgage Ready Data".
U.S. Appl. No. 62/581,356, filed Nov. 3, 2017, "Identifying Multiple Mortgage Ready Properties".
U.S. Appl. No. 62/581,373, filed Nov. 3, 2017, "Incentivizing an Agent Based Upon Mortgage Ready Data Updated".
U.S. Appl. No. 62/581,391, filed Nov. 3, 2017, "Approving and Updating Dynamic Mortgage Applications".
U.S. Appl. No. 62/581,423, filed Nov. 3, 2017, "Continuously Monitoring and Updating Mortgage Ready Data".
U.S. Appl. No. 62/581,442, filed Nov. 3, 2017, "Identifying Multiple Mortgage Ready Properties".
U.S. Appl. No. 62/581,470, filed Nov. 3, 2017, "Incentivizing an Agent Based Upon Mortgage Ready Data Updated".
U.S. Appl. No. 62/581,480, filed Nov. 3, 2017, "Approving and Updating Dynamic Mortgage Applications".
U.S. Appl. No. 62/581,494, filed Nov. 3, 2017, "Continuously Monitoring and Updating Mortgage Ready Data".
U.S. Appl. No. 62/581,521, filed Nov. 3, 2017, "Identifying Multiple Mortgage Ready Properties".
U.S. Appl. No. 62/581,524, filed Nov. 3, 2017, "Incentivizing an Agent Based Upon Mortgage Ready Data Updated".
U.S. Appl. No. 62/584,364, filed Nov. 10, 2017, "Blockchain Subrogation Payments".
U.S. Appl. No. 62/584,435, filed Nov. 10, 2017, "Fault Determination of Blockchain Subrogation Claims".
U.S. Appl. No. 62/589,444, filed Nov. 21, 2017, "Technology for Building and Managing Data Models".
U.S. Appl. No. 62/592,975, filed Nov. 30, 2017, "Technology for Building and Managing Data Models".
U.S. Appl. No. 62/593,727, filed Dec. 1, 2017, "Risk Mitigation for Affinity Groupings".
U.S. Appl. No. 62/595,803, filed Dec. 7, 2017, "Evidence Oracles".
U.S. Appl. No. 62/595,823, filed Dec. 7, 2017, "Using a Distributed Ledger for Subrogation Recommendations".
U.S. Appl. No. 62/598,246, filed Dec. 13, 2017, "Using a Distributed Ledger for Line Item Determination".
U.S. Appl. No. 62/599,103, filed Dec. 15, 2017, "Residence Provisioning Platform".
U.S. Appl. No. 62/609,611, filed Dec. 22, 2017, "Using a Vehicle Mode for Subrogation on a Distributed Ledger".
U.S. Appl. No. 62/609,644, filed Dec. 22, 2017, "Using a Historical Data for Subrogation on a Distributed Ledger".
U.S. Appl. No. 62/609,786, filed Dec. 22, 2017, "Vehicle Creation of a Subrogation Distributed Ledger".
U.S. Appl. No. 62/609,800, filed Dec. 22, 2017, "Using a Distributed Ledger to Detemine Fault in Subrogation".
U.S. Appl. No. 62/615,286, filed Jan. 9, 2018, "Technology for Building and Managing Data Models".
U.S. Appl. No. 62/617,824, filed Jan. 16, 2018, "Residence Provisioning Platform".
U.S. Appl. No. 62/618,955, filed Jan. 18, 2018, "Residence Provisioning Platform".
U.S. Appl. No. 15/870,292, Nonfinal Office Action, dated Dec. 31, 2019.
U.S. Appl. No. 15/87,350, Nonfinal Office Action, dated Oct. 10, 2019.
U.S. Appl. No. 15/870,364, Nonfinal Office Action, dated Oct. 9, 2019.
U.S. Appl. No. 15/870,371, Nonfinal Office Action, dated Aug. 28, 2019.
Van Oerle et al., "Distributed ledger technology for the financial industry, Blockchain Administration 3.0", White Paper, Robeco (May 2016).
Haber & Stornetta, "How to Time-Stamp a Digital Document", Bellcore, NJ (1991).
Mazieres and Shasha, "Building secure file systems out of Byzantine storage", NYU (2002).
BlockstreetHQ Team, "Before Blockchain, There was Distributed Ledger Technology BlockstreetHQ," Medium.com (2018).
Sneakernet, definition, Wikipedia. Retrieved from the Internet at: <https://en.wikipedia.org/wiki/Sneakernet> (2020).
File Transfer Protocol, definition/history/overview, Wikipedia. Retrieved from the Internet at: <https://en.wikipedia.org/wiki/File Transfer Protocol> (2020).

(56) References Cited

OTHER PUBLICATIONS

Distribution File system overview. Retrieved from the Internet at: <http://www.cse.chalmers.se/~tsigas/Courses/DCDSeminar/Files/afs_report.pdf> (2020).

Authors et al.: Disclosed Anonymously, "Mechanism to Preserve Audit History Record for Insurance Claim Using Blockchain Smart Contract", An IP.com Prior Art Database Technical Disclosure (2016).

C.L.U.E. ® Personal Property, "How to Read Your Rreport", ChoicePoint (1999).

Goodman et al., "Clue Reports Comprehensive Loss Underwriting Reports", Clue, Apr. 1, 2003.

Azaria et al., MedRec: Using blockchain for medical data access and permission management, 2016 2nd International Conference on Open and Big Data, pp. 25-30 (2016).

Gatteschi et al., Blockchain and smart contracts for insurance: is the technology mature enough?, Future Internet, 10,20 (2018).

Antonopoulos, Mastering Bitcoin: Unlocking Digital Crypto-Currencies, Sebastopol, California: O'Reilly Media, Inc., 282 pp. (2010).

Lorenz et al., Blockchain in Insurance—Oportunity or Threat, Jul. 2016, pp. 1-9 (Year: 2016).

* cited by examiner

800

DISTRIBUTED LEDGER SYSTEM FOR MANAGING SMART VEHICLE DATA

CROSS-REFERENCE TO RELATED APPLICATIONS

The present disclosure is a continuation of (i) U.S. patent application Ser. No. 15/870,350, titled "Distributed Ledger System for Managing Smart Vehicle Data," filed Jan. 12, 2018; and claims priority to and the benefit of: (ii) U.S. Provisional Patent Application No. 62/500,049, titled "Distributed Ledger Systems," filed on May 2, 2017; and which claims the benefit of (iii) U.S. Provisional Patent Application No. 62/500,326, titled "Distributed Ledger System," filed on May 2, 2017; (iv) U.S. Provisional Patent Application No. 62/508,133, titled "Distributed Ledger System for Managing Smart Home Data, Vehicle Data, Insurance Claim Payouts, and/or Insurance Carrier Discovery," filed on May 18, 2017; (v) U.S. Provisional Patent Application No. 62/545,262, titled "Distributed Ledger System for Managing Loss Histories," filed on Aug. 22, 2017; (vi) U.S. Provisional Patent Application No. 62/548,668, titled "Distributed Ledger System for Managing Vehicle Sensor Data Utilized to Develop Collision Profiles," filed on Aug. 22, 2017; (vii) U.S. Provisional Patent Application No. 62/548,679, titled "Distributed Ledger System for Use with Vehicle Sensor Data and Usage Based Systems," filed on Aug. 22, 2017; (viii) U.S. Provisional Patent Application No. 62/548,682, titled "Distributed Ledger System for Managing Medical Records," filed on Aug. 22, 2017; (ix) U.S. Provisional Patent Application No. 62/548,692, titled "Distributed Ledger System for Insurance Record Management Systems," filed on Aug. 22, 2017; (x) U.S. Provisional Patent Application No. 62/548,741, titled "Distributed Ledger System for Smart Home Data," filed on Aug. 22, 2017; (xi) U.S. Provisional Patent Application No. 62/548,700, titled "Distributed Ledger System for Managing Smart Vehicle Data," filed on Aug. 22, 2017; (xii) U.S. Provisional Patent Application No. 62/548,731, titled "Distributed Ledger System for Claim Payouts," filed on Aug. 22, 2017; and (xiii) U.S. Provisional Patent Application No. 62/548,748, titled "Distributed Ledger System for Carrier Discovery," filed on Aug. 22, 2017; the entire disclosures of which are expressly incorporated herein by reference.

TECHNICAL FIELD

Systems and methods are disclosed with respect to using a distributed ledger for managing smart vehicle data.

BACKGROUND

Generally speaking, companies may utilize centralized databases or servers for a number of purposes. For example, a "smart vehicle" that has sensors and computer systems may have a network connection enabling the smart vehicle to communicate with a centralized server. Generally speaking, this data stored at the centralized server may not be readily accessible by the owner of the smart vehicle and/or by third parties that might otherwise be authorized to access the data.

BRIEF SUMMARY

In one aspect, a computer-implemented method for tracking vehicle events may include any one or more of the following: (A) configuring or implementing a plurality of servers, each of the plurality of servers maintaining a copy of a distributed ledger; (B) performing the following when a vehicle event pertaining to a vehicle is detected: (i) generating, at a first server from the plurality of servers, a transaction record including data corresponding to the vehicle event; (ii) proposing the transaction record to one or more other servers from the plurality of servers; (iii) performing, via the plurality of servers, a consensus analysis of the transaction record utilizing a consensus mechanism; and/or (iv) when the consensus analysis indicates that the plurality of servers have formed a consensus, storing the transaction record at the distributed ledger by storing the transaction record to each copy of the distributed ledger at the plurality of servers; and/or (C) performing an insurance function based upon the transaction record stored to the distributed ledger. The transaction may be stored to a blockchain on the distributed ledger. The method may include additional, less, or alternate actions, including those discussed elsewhere herein.

Advantages will become more apparent to those of ordinary skill in the art from the following description of the preferred aspects, which have been shown and described by way of illustration. As will be realized, the present aspects may be capable of other and different aspects, and their details are capable of modification in various respects. Accordingly, the drawings and description are to be regarded as illustrative in nature and not as restrictive.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

There are shown in the drawings arrangements which are presently discussed, it being understood, however, that the present embodiments are not limited to the precise arrangements and instrumentalities shown, wherein.

Figure 1A:
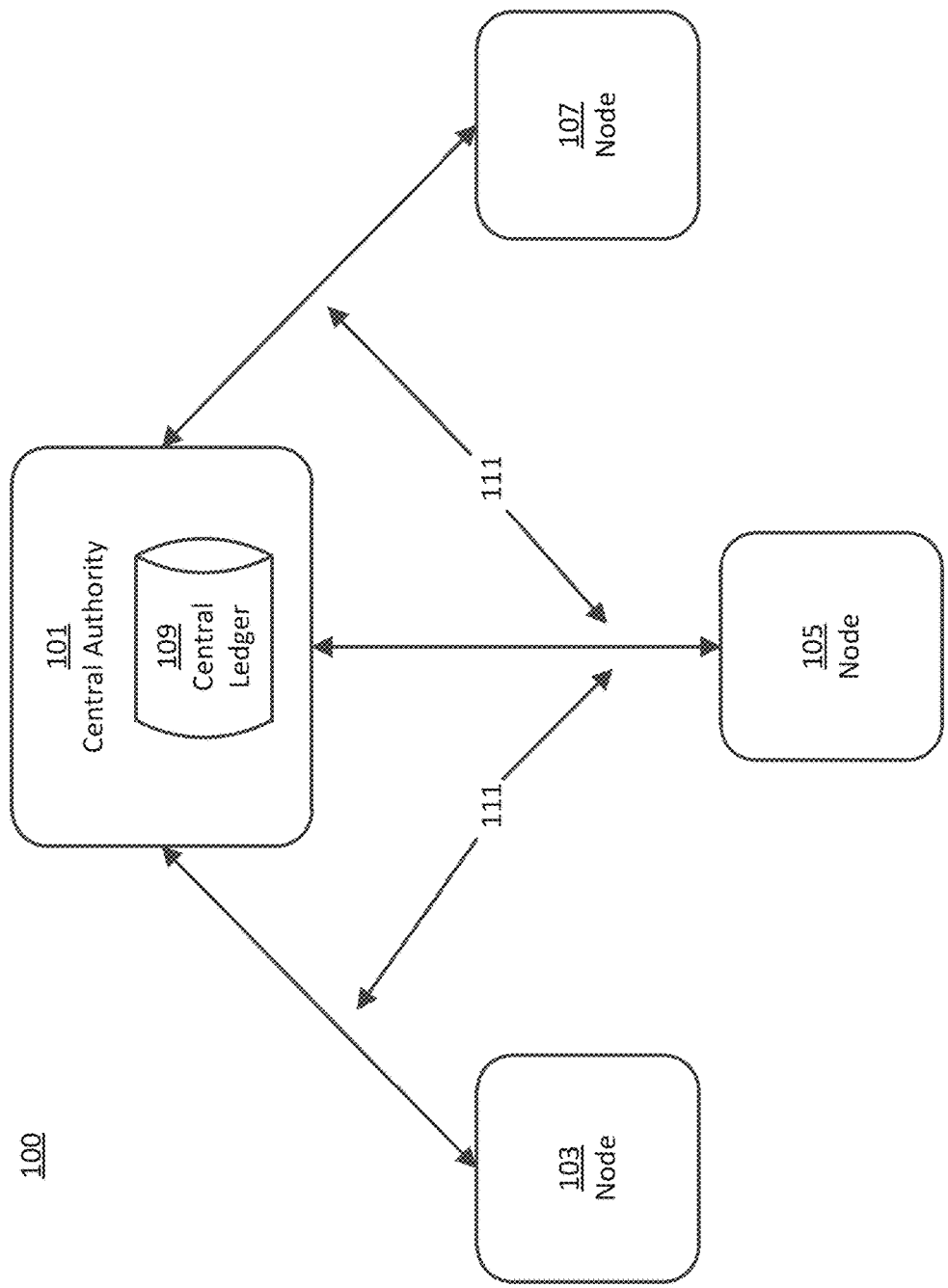
FIG. 1A depicts an exemplary database system in accordance with one aspect of the present disclosure.

The figures depict aspects of the present embodiments for purposes of illustration only. One skilled in the art will readily recognize from the following discussion that alternate aspects of the structures and methods illustrated herein may be employed without departing from the principles of the invention described herein.

DETAILED DESCRIPTION

The present embodiments relate to, inter alia, systems and methods for using a distributed ledger to record information related to processes and services in the healthcare, automotive, and real estate industries. For example, a distributed ledger may be used to track and/or manage: (i) smart home and/or smart vehicle data; (ii) insurance claim payment activity; and/or (iii) insurance carrier discovery. In some embodiments, the distributed ledger is a blockchain system. The systems and methods described herein allow for using a distributed ledger which gives the option for private information, and permissioned participants in the blockchain. In particular, the systems and methods allow for a distributed consensus amongst businesses, consumers, and authorities, as to the validity of information and transactions stored on the distributed ledger.

The above listed examples, and disclosed systems and methods, may use an application of distributed ledgers, where each new block may be cryptographically linked to the previous block in order to form a "blockchain."

A blockchain is a way of achieving a distributed consensus on the validity or invalidity of information. As opposed to using a central authority, a blockchain is a distributed database, or ledger, in which transactional records are maintained at each node of a peer to peer network. Commonly, the distributed ledger is comprised of groupings of "transactional records" (sometimes simply referred to as "transactions") bundled together into a "block." Generally speaking, each "transaction" or "transactional record" is a record of an update or change made to the distributed ledger. The nature of the information included in each transactional record generally depends on the particular implementation of a given distributed ledger, and on the information the distributed ledger is intended to track.

Every creation or lookup of a transaction may be associated with a real-world "event." For example, a distributed ledger may track a currency, wherein each transaction includes data identifying two parties and an amount of currency exchanged between the two parties. In such an example, the real-world "event" associated with the creation of the transaction is an exchange of currency between the two parties.

When a change to the distributed ledger is made (e.g., when a new transaction and/or block is created), each node must form a consensus as to how the change is integrated into the distributed ledger. Upon consensus, the agreed upon change is pushed out to each node so that each node maintains an identical copy of the updated distributed ledger. Any change that does not achieve a consensus is ignored. Accordingly, unlike a traditional system which may use a central authority, a single party cannot unilaterally alter the distributed ledger. This inability to modify past transactions lead to blockchains being generally described as trusted, secure, and immutable.

Some blockchains may be deployed in an open, decentralized, and permissionless manner meaning that any party may view information, submit new information, or join the blockchain as a node responsible for confirming information. This open, decentralized, and permissionless approach to a blockchain has limitations. As an example, these blockchains may not be good candidates for interactions that require information to be kept private, such as information related to a vehicle lifecycle process, or for interactions that require all participants to be vetted prior to their participation.

In any event, to create a new block, each transaction within a block may be assigned a hash value (i.e., an output of a cryptographic hash function, such as SHA-256 or MD5). These hash values may then be combined together utilizing data storage and cryptographic techniques (e.g., a Merkle Tree) to generate a hash value representative of the entire new block, and consequently the transactions stored in the block. This hash value may then be combined with the hash value of the previous block to form a hash value included in the header of the new block, thereby cryptographically linking the new block to the blockchain. To this end, the precise value utilized in the header of the new block may be dependent on the hash value for each transaction in the new block, as well as the hash value for each transaction in every prior block.

According to certain aspects disclosed herein, information stored in blockchains may be trusted, because the hash value generated for the new block and a nonce value (an arbitrary number used once) are used as inputs into a cryptographic puzzle. The cryptographic puzzle may have a difficulty set by the nodes connected to the blockchain network, or the difficulty may be set by administrators of the blockchain network. In one example of the cryptographic puzzle, a solving node uses the hash value generated for the new block and repeatedly changes the value of the nonce until a solution for the puzzle is found. For example, finding the solution to the cryptographic puzzle may involve finding the nonce value that meets certain criteria (e.g., the nonce value begins with five zeros).

When a solution to the cryptographic puzzle is found, the solving node publishes the solution and the other nodes then verify that the solution is valid. Since the solution depends on the particular hash values for each transaction within the blockchain, if the solving node attempted to modify any transaction stored in the blockchain, the solution would not be verified by the other nodes. More specifically, if a single node attempts to modify a prior transaction within the blockchain, a cascade of different hash values may be generated for each tier of the cryptographic combination technique. This results in the header for one or more blocks being different than the corresponding header(s) in every other node that did not make the exact same modification.

Exemplary Database & Distributed Ledger

FIG. 1A depicts an exemplary central authority database system 100 in accordance with one aspect of the present disclosure. FIG. 1A includes a central authority 101; a plurality of nodes 103, 105, and 107; a central ledger 109; and a plurality of network connections 111. In one exemplary operation of the database system 100, one of the nodes, for example node 103, issues a request to the central authority 101 to perform an action on data stored in the central ledger 109. This request may be a request to create, read, update, or delete data that is stored in the central ledger 109.

In such an example, the central authority 101 receives the request, processes the request, makes any necessary changes to the data stored in the central ledger 109, and informs the requesting node (node 103) of the status of the request. The central authority 101 may also send out status updates to the other nodes on the network about the change made, if any, to the data by node 103. In the database system 100, all interaction with the data stored in the central ledger 109 occurs through the central authority 101. In this way, the central authority functions as a gatekeeper of the data.

Accordingly, the central authority 101 may operate as a single point of entry for interacting with the data, and consequently the central authority 101 is a single point of failure for the entire database system 100. As such, if the central authority 101 is not accessible to the nodes in the database system 100, then the data stored in the central ledger 109 is not accessible. In another example, each individual node may keep its own databases and may periodically send a copy of its database to the central authority 101, where the received databases are reconciled to form a single cohesive record of the data stored in the central ledger 109.

Figure 1B:
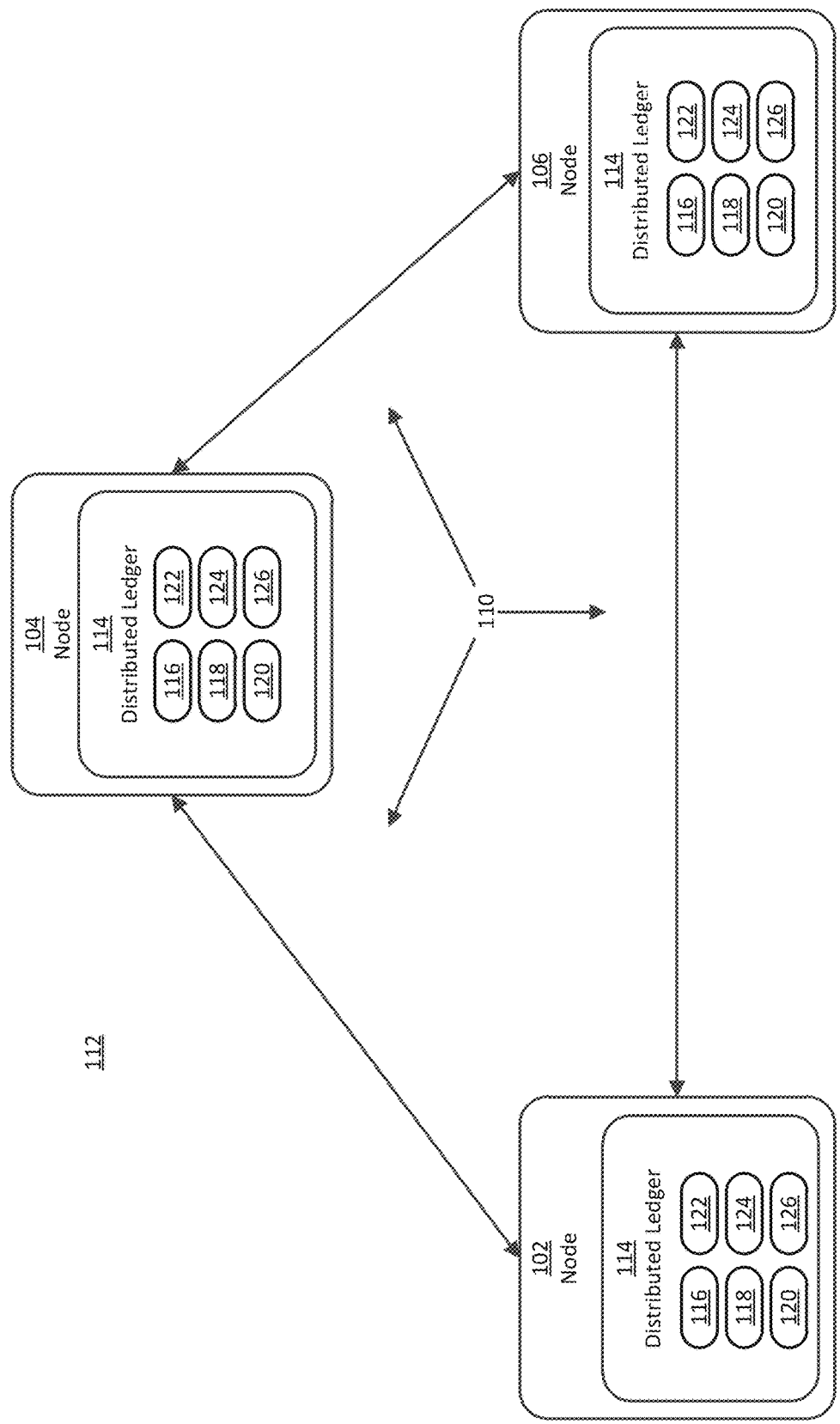
FIG. 1B depicts an exemplary distributed ledger system in accordance with one aspect of the present disclosure.

Conversely, FIG. 1B depicts an exemplary distributed ledger system 112 in accordance with an aspect of the present disclosure. An example of a distributed ledger system 112 is the blockchain system described above. FIG. 1B includes a plurality of nodes 102, 104, and 106; a distributed ledger 114; and a plurality of network connections 110. In the distributed ledger system 112, each node keeps a copy of the distributed ledger 114.

Each copy of the distributed ledger 114 maintains a copy of a plurality of transactions 116-126 tracked in the distributed ledger 114. Generally speaking, each of the transactions 116-126 (sometimes referred to as a "transactional records" or "transaction records") is a record of an update or change made to the distributed ledger 114. The nature of the information included in each transactional record 116-126 generally depends on the particular implementation of the distributed ledger 114, and on the information the distributed ledger 114 is intended to track.

As changes are made to the distributed ledger 114, each node 102-106 updates its copy of the distributed ledger 114. A consensus mechanism (sometimes referred to as a consensus protocol) may be used by the nodes in the distributed ledger system 112 to decide when it is appropriate to make changes to the distributed ledger 114. Example consensus mechanisms that may be used by the distributed ledger 114 include: proof of work, proof of stake, proof of activity, proof of burn, proof of capacity, and/or proof of elapsed time. Therefore, each node has its own copy of the distributed ledger 114, which is identical to every other copy of the distributed ledger 114 stored by each other node. The distributed ledger system 112 is more robust than a central authority database system such as the system 100 shown in FIG. 1A, because the distributed ledger system 112 is decentralized and no single point of failure exists.

The system 112 and distributed ledger 114 may be implemented using a number of different blockchain protocols, depending on the embodiment. Example blockchain protocols that may be implemented include: Hyperledger Fabric, Ethereum, Corda, Ripple, ZCash, and Sawtooth. For example, the method 600 described with reference to FIG. 6A may be implemented to track loss history using the distributed ledger 114 in an embodiment in which the distributed ledger 114 is configured to utilize the Hyperledger Fabric protocol.

Figure 1C:
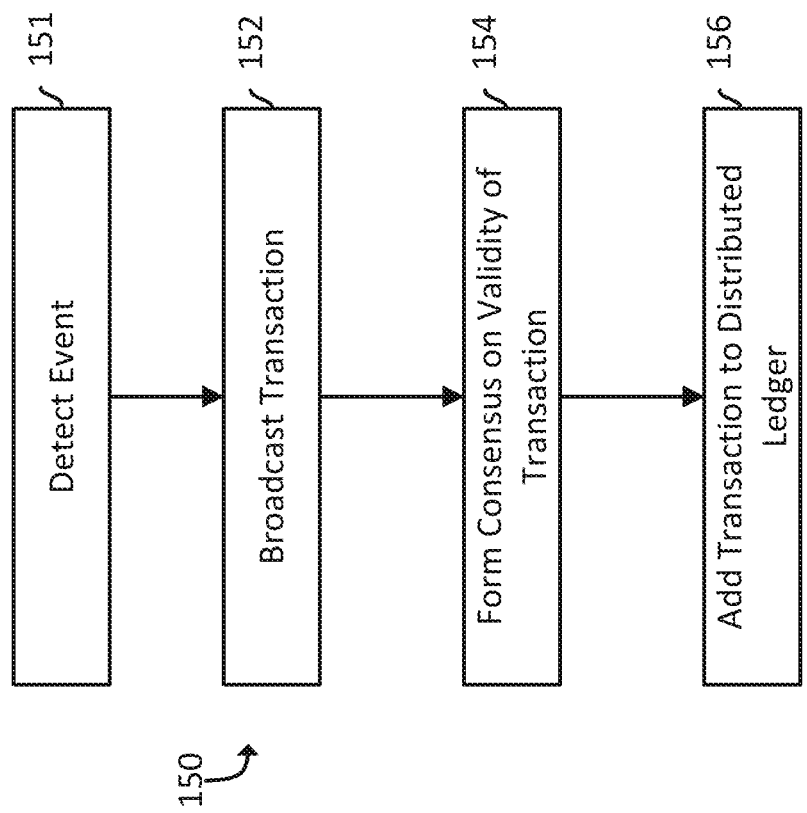
FIG. 1C depicts an exemplary computer-implemented method for adding a transaction to a distributed ledger in accordance with one aspect of the present disclosure.

FIG. 1C is a flow chart of an exemplary computer-implemented method 150 for adding a transaction to the distributed ledger 114 in accordance with one aspect of the present disclosure. The method 150 may be implemented, in whole or in part, by the nodes 102-106 in the system 112 shown in FIG. 1B, and may be saved to a memory of one or more of the nodes as one or more instructions or routines executable by a processor.

The method 150 may begin when an event is detected. The event may be any suitable trigger that results in the distributed ledger 114 being accessed and/or updated, and may vary depending on the implementation. For example, depending on the embodiment, the event may be: (i) a home event pertaining to an insured home (such as the collection of new sensor data at the home, or of new insurance claim activity involving the home), (ii) a vehicle event (such as the collection of new sensor data at or by the vehicle, or of new insurance claim activity involving the vehicle), (iii) a payment event pertaining to an insurance claim, or (iv) an insurance event pertaining to an insured individual and/or policies carried by that individual.

After the event occurs, data pertaining to the event may be generated and/or collected, and a transaction including and/or representing the data may be generated. A node may broadcast the transaction (block 152). The nature of the transaction depends on the implementation. In one embodiment, the ledger 114 tracks home events, and each home event may represent collected sensor data (e.g., from a smart thermostat, carbon monoxide detector, home computer, intelligent personal assistant, etc.) and/or data representing new insurance claim activity (e.g., the filing of a new claim, the generation of an estimate, the payment of a claim, etc.). The transaction might include data about the property (e.g., property type, address of a home, type of data collected, etc.), owner (e.g., name, social security number, etc.), and/or claim (damage type, estimated loss, claim payout amount, etc.).

One or more other nodes in the system 112 may receive the broadcasted transaction and attempt to form a consensus in order to verify the validity of the transaction (block 154). The nodes may utilize a proof of work consensus protocol such as that already described. If the nodes are unable to reach consensus, the transaction is not added to the ledger 114. When the nodes reach consensus, the transaction is added to the distributed ledger 156. That is, a copy of the transaction is added to each copy of the ledger 114 held at each node 102-106. Accordingly, the nodes 102-106 are able to maintain identical copies of the ledger 114, thus maintaining consistency and accuracy of the ledger 114 without a single central authority.

Exemplary Transaction Flow & Block Propagation Flow

Figure 2A:
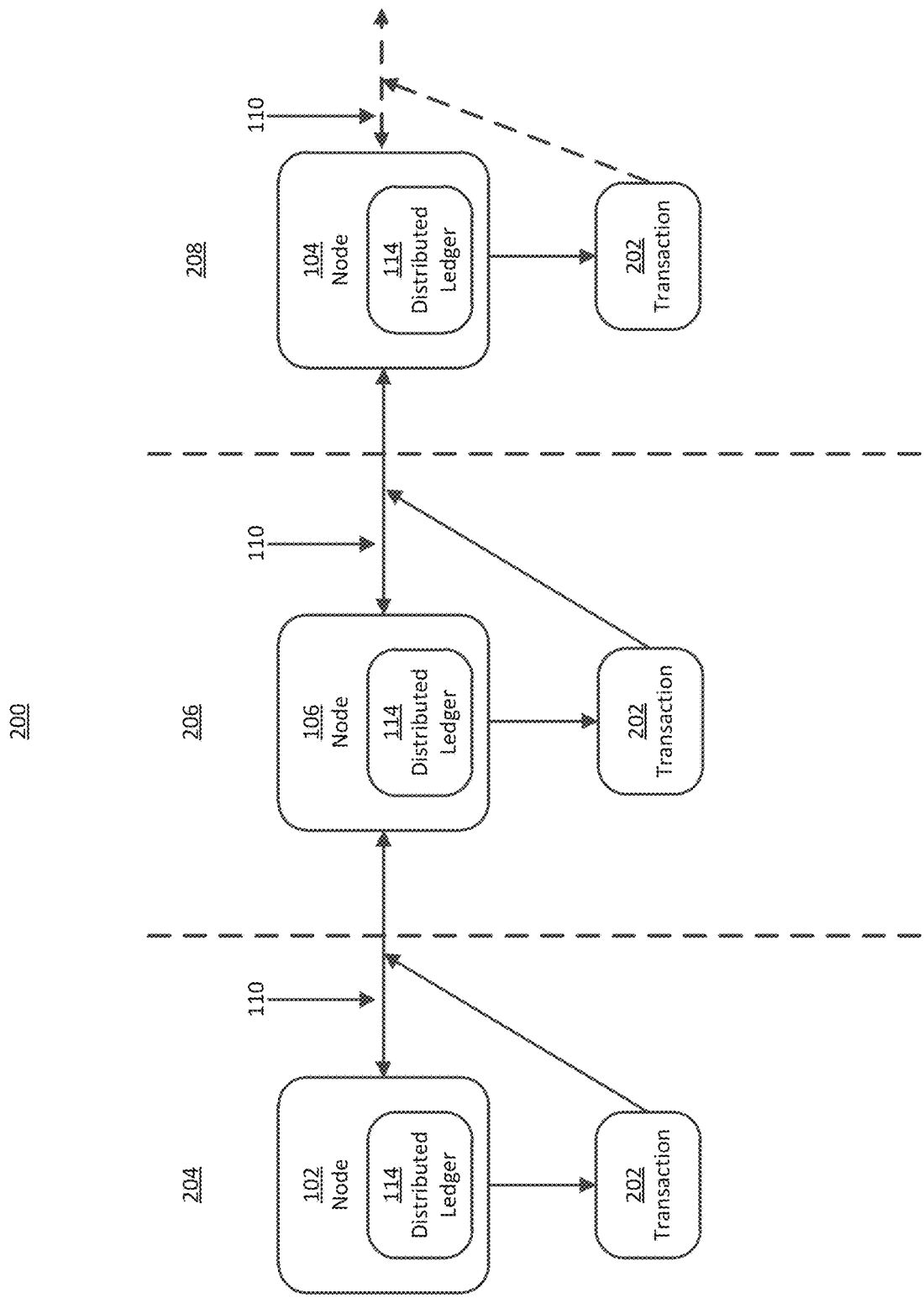
FIG. 2A depicts an exemplary transaction flow in accordance with one aspect of the present disclosure.

FIG. 2A depicts an exemplary transaction flow 200 in accordance with one aspect of the present disclosure. FIG. 2A includes a transactional record ("transaction") 202; three different time frames 204, 206, and 208; the nodes 102-106; the network connections 110; and the distributed ledger 114. The transaction flow 200 may represent a sequential flow of the transaction 202 through a network (such as the network depicted in FIG. 1B).

In the shown example, the node 102 generates the transaction 202 at time 204. The transaction 202 may include data that is stored in the distributed ledger 114 at the node 102, or may include data received by the node 102 from outside the distributed ledger 114. The node 102 may transmit the newly generated transaction 202 to node 106 via the network connection 110.

At time 206, the node 106 receives the transaction 202, and confirms that the information contained therein is correct. If the information contained in the transaction 202 is not correct, the node 106 may reject the transaction and not propagate the transaction 202 through the system. If the information contained in the transaction 202 is correct, the node 106 may transmit the transaction 202 to the node 104.

At time 208, the node 104 may receive the transaction 202 and may confirm or reject the transaction 202. In some embodiments, the node 104 may not transmit the confirmed transaction 202, because there are no further nodes to transmit to, or all the nodes in the network have already received transaction 202.

In some embodiments, at any of time frames 204, 206, or 208, any of the nodes may add the confirmed transaction 202 to their copy of the distributed ledger 114, or to a block of transactions stored in the distributed ledger 114. In some embodiments, confirming the transaction 202 includes checking cryptographic key-pairs for participants involved in the transaction 202. Checking the cryptographic key-pairs may follow a method laid out by a consensus protocol, such as the consensus protocol discussed in FIG. 1B.

Figure 2B:
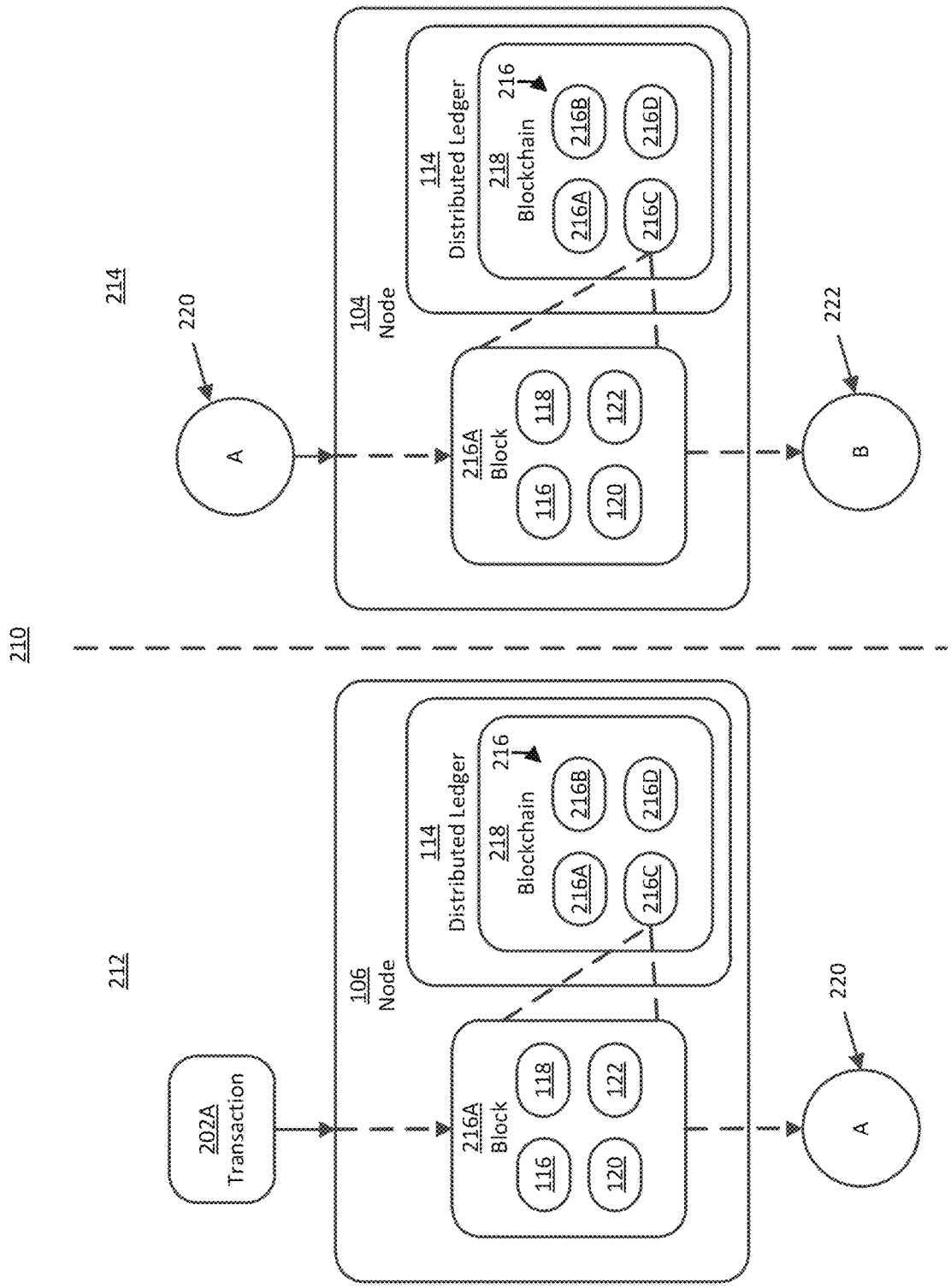
FIG. 2B depicts an exemplary block propagation flow in accordance with one aspect of the present disclosure.

FIG. 2B depicts an exemplary block propagation flow 210 in accordance with one aspect of the present disclosure. FIG. 2B includes two time frames 212 and 214; the node 106 and the node 104; the transactions 116-122; a set of blocks of transactions 216A-216D; the distributed ledger 114; and a blockchain 218. The block propagation flow 210 may follow the blockchain system described above, or may follow another blockchain propagation algorithm.

The block propagation flow 210 may begin with the node 106 receiving the transaction 116 at time 212. When node 106 confirms that the transaction 116 is valid, the node 106 may add the transaction 116 to the block 216A (which may be newly generated). As part of adding the transaction 116 to the block 216A, node 106 may solve a cryptographic puzzle and include the solution in the newly generated block 216A as proof of the work done to generate the block 216A. This proof of work may be similar to the proof of work described above which utilizes guessing a nonce value. In other embodiments, the transaction 116 may be added to a pool of transactions until enough transactions exist to form a block. Node 106 may transmit the newly created block 216A to the network at 220. Before or after propagating the block 216A, node 106 may add the block 216A to its copy of the blockchain 218.

At time 214, node 104 may receive the block 216A. Node 104 may verify that the block 216A is valid by checking the solution to the cryptographic puzzle provided in the block 216A. If the solution is accurate, then the node 104 may add the block 216A to its blockchain 218 and transmit the block 216A to the rest of the network at 222.

In one embodiment, one or more transactions 202 or events may relate to: smart contracts, loss history and loss history reports, insurance claims, vehicle sensor data, medical records, and/or insurance records.

Figure 2C:
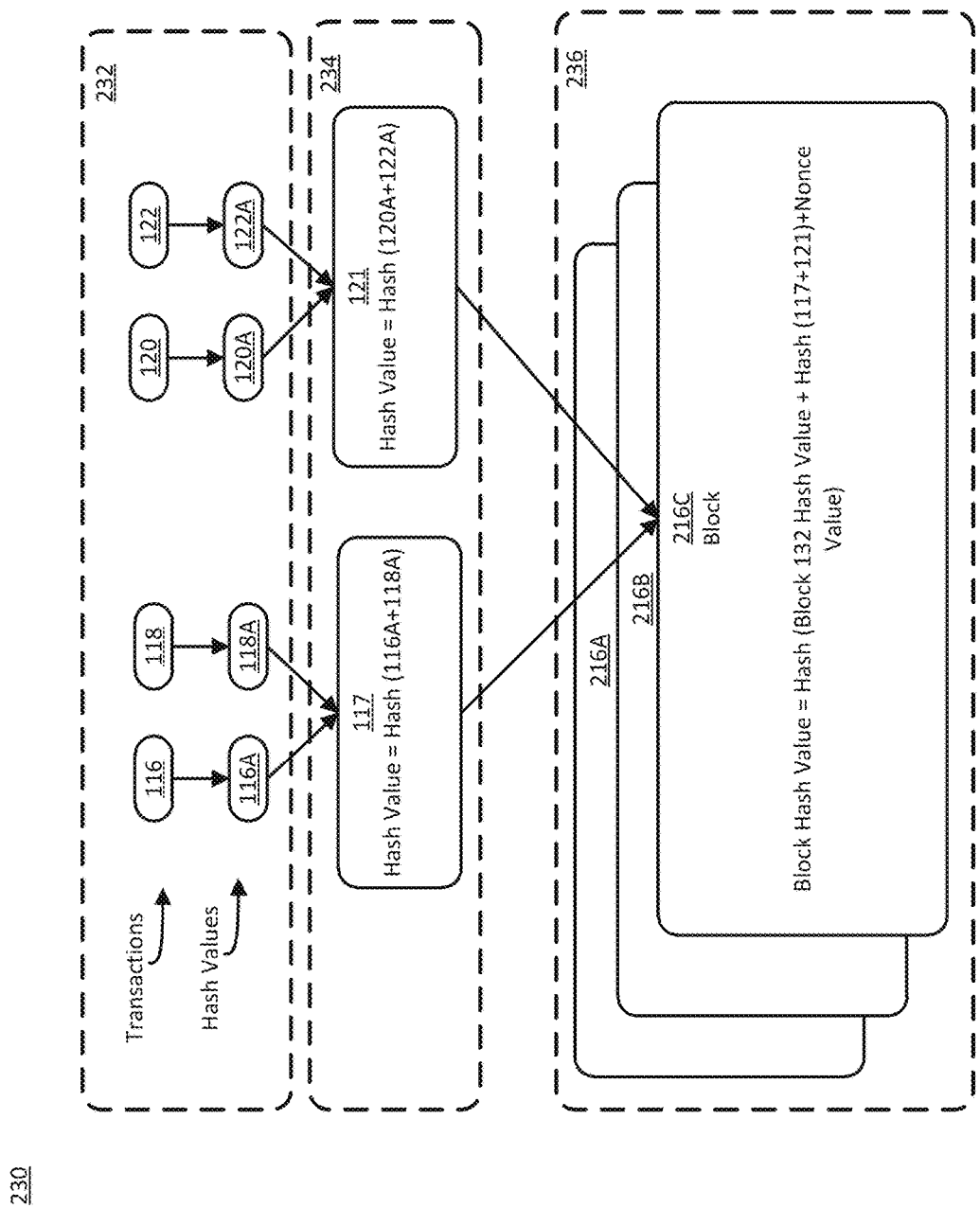
FIG. 2C depicts an exemplary computer-implemented method for generating a block in a blockchain in accordance with one aspect of the present disclosure.

FIG. 2C depicts an exemplary method 230 for generating the block 216C shown in FIG. 2B, according to one embodiment. The method 230 may be implemented by a processor of one or more of the nodes 102-106, and may be implemented as part of a consensus mechanism. It will be understood that the method 230 is exemplary, and not every embodiment implements the method 230.

In the method 230, a processor generates hash values 116A-122A for each of the transactions 116-122, using data associated with each of the transactions 116-122 as inputs for a hash function (step 232). The processor then generates a hash value 117 using the hash values 116A and 118A as inputs for the hash function, and a hash value 121 using the hash values 120A and 122A as inputs for the hash function (step 234). Finally, when generating block 216C, a hash for block 216 is generated using as inputs: a hash value of the "chained" block 216B, the hash vales 117 and 121, and a nonce value (step 236). Because every other node may have access to the block 216B and to the transactions 116-122, when a node publishes that a cryptographic puzzle has been solved utilizing the nonce value, the other nodes can confirm whether or not the solution is valid (because a change to any transaction 116-122, or to any transaction in block 216B, or to the nonce value, will result in a different hash value for block 216C).

Exemplary Sequence Diagram

Figure 3:
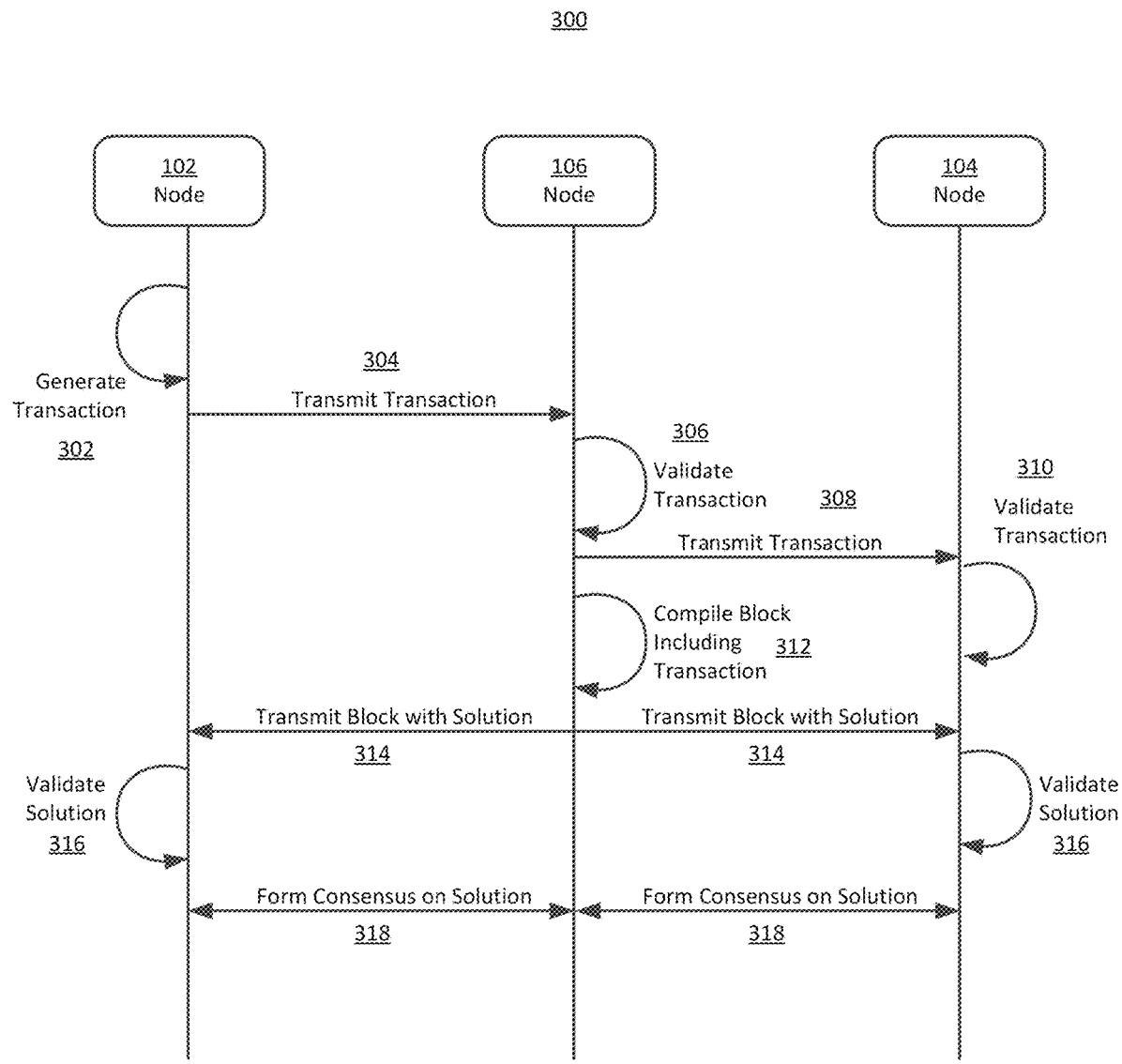
FIG. 3 depicts an exemplary sequence diagram in accordance with one aspect of the present disclosure.

FIG. 3 depicts an exemplary sequence diagram 300 in accordance with one aspect of the present disclosure. FIG. 3 includes the set of nodes 102, 104, and 106. At time 302, the node 102 may generate a transaction. At time 304, the transaction may be transmitted from the node 102 to the node 106. At time 306, the node 106 may validate the transaction. At time 308, if the transaction is valid, the node 106 may transmit the transaction to node 104. At time 310, node 104 may validate the transaction. At time 312, the node 106 may compile a block including the validated transaction. Compiling a block may include generating a solution to a cryptographic puzzle and linking the block to other blocks, as described in the embodiments above. At time 314, once the block is compiled, the node 106 may transmit the block with the solution to both the node 102 and the node 104.

At time 316, both nodes may validate the solution to the block. Verifying may include checking a cryptographic key-pair as described above. At time 318, the three nodes form a consensus that the solution is valid. Accordingly, in the shown example, all the nodes have formed a consensus on the blocks of transactions stored by all the nodes.

Exemplary Node

Figure 4:
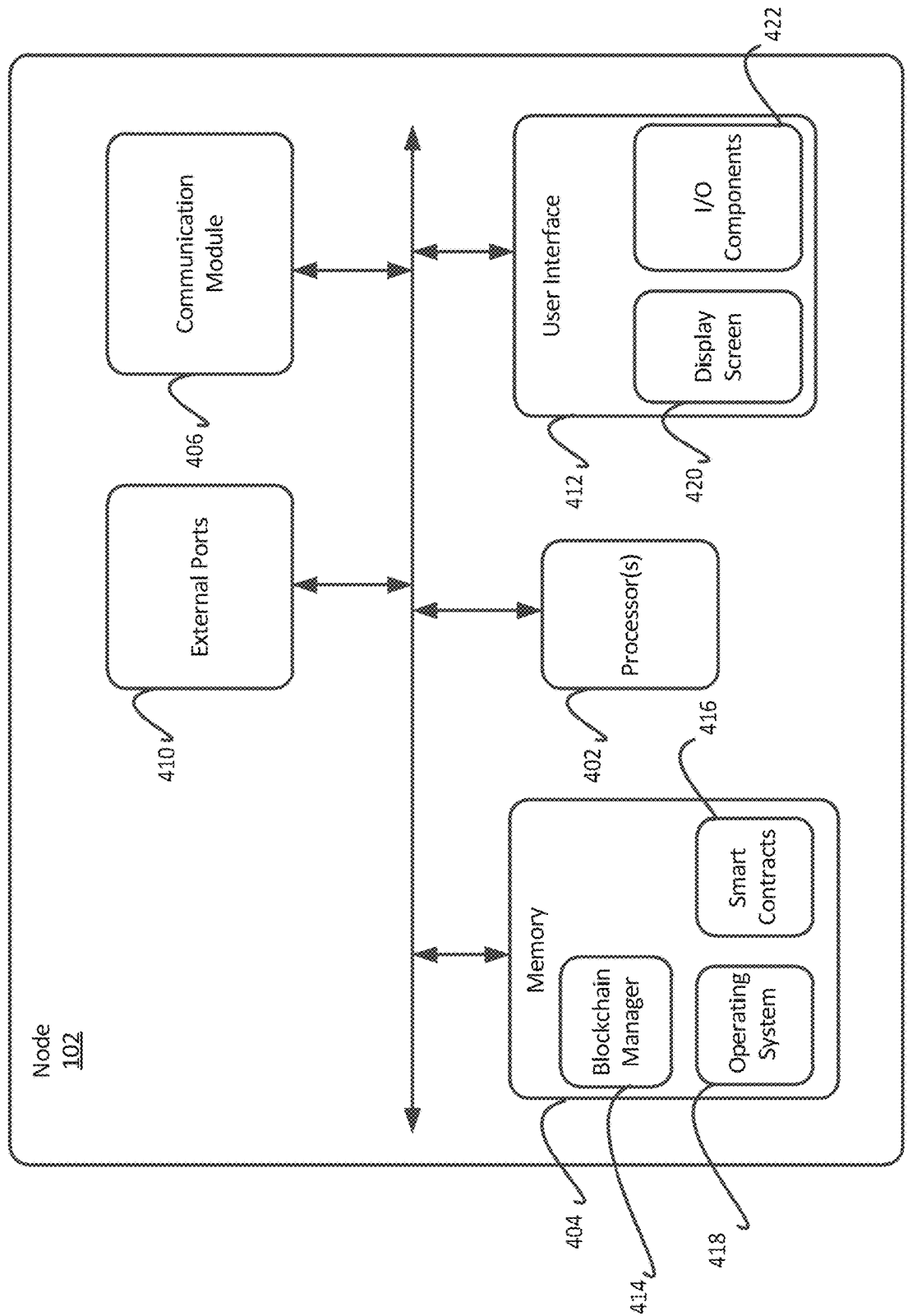
FIG. 4 depicts an exemplary node in accordance with one aspect of the present disclosure.

FIG. 4 is a block diagram of a node 102, according to one embodiment. It will be understood that the nodes 104 and 106 may perform one or more of the functions that the node 102 is capable of performing, and may include one or more of the components included in the node 102. The node 102 may utilize the decentralized system 112 described with respect to FIG. 1B, the flows 200 and 210 of transactions and blocks described in FIGS. 2A and 2B, and/or the blockchain system 500 described below with reference to FIG. 5.

The node 102 includes one or more of the following: at least one processor 402, memory 404, a communication module 406, one or more external ports 410, a user interface 412, a blockchain manager 414, smart contracts 416, an operating system 418, a display screen 420, and input/output components 422. In some embodiments, the node 102 may generate a new block of transactions using the blockchain manager 414. Similarly, the node 102 may use the blockchain manager 414 in conjunction with the smart contracts 416 stored in memory 404 to execute the functionality disclosed herein.

In some embodiments, the smart contracts 416 operate independent of the blockchain manager 414 or other applications. In some embodiments, the node 102 does not include one or more of the blockchain manager 414 or the smart contracts 416. In some embodiments, the node 102 may have additional or less components than what is described. The smart contracts may relate to, or be associated with, insureds and/or insured assets, including smart insurance contracts, smart maintenance contracts, smart health care contracts, smart repair or upkeep contracts, etc.

The node 102, as part of a decentralized ledger system 112, or another decentralized or centralized network, may be used to handle systems that interact with and manipulate data and transactions designed for tracking loss history, vehicle sensor data, medical records, and/or insurance records.

Exemplary Blockchain System

Figure 5:
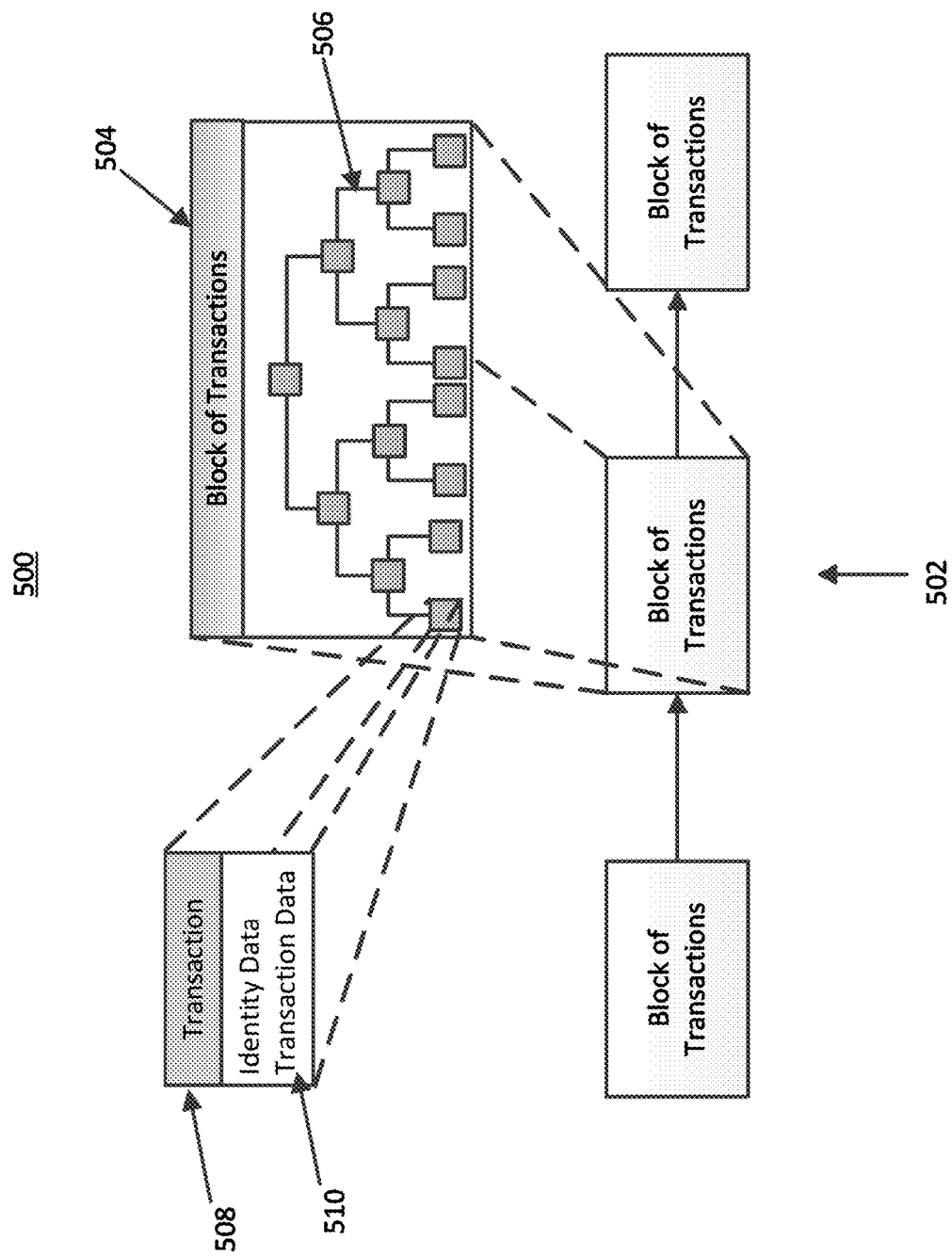
FIG. 5 depicts an exemplary blockchain in accordance with one aspect of the present disclosure.

FIG. 5 depicts an exemplary blockchain system 500 in accordance with an aspect of the present disclosure. The system 500 includes a blockchain 502 that includes one or more blocks, including a block of transactions 504. The block 504 includes a Merkle Tree 506 that includes one or more transactions, including a transaction 508 that includes data 510. The Merkle Tree 506 may be the same Merkle Tree referred to above that cryptographically links transactions together. In some embodiments, the blockchain system 500 may utilize other methods of organizing transactions in a block.

As noted, the block of transactions 504 includes the transaction 508, but may also include other transactions in some instances. In some embodiments, the block of transactions 504 has a size limit limiting the number of transactions that the block 504 may store. In one exemplary implementation, the block 504 includes a reference to a previous block of transactions that was added to the blockchain 502 prior to the block 504 being added to the blockchain 502. As such, and as described above, each block in the blockchain 502 is linked to every other block in the blockchain 502.

In some embodiments, the block of transactions 504 may organize the transactions it has received into a Merkle Tree 506 to facilitate access to the stored transactions. The transactions may be hashed using a cryptographic hash algorithm, such as the algorithms discussed above, and the hash of each transaction may be stored in the tree. As the tree is constructed, the hash of each adjacent node at the same level is hashed together to create a new node that exists at a higher level in the tree. Therefore, the root of the tree, or the node at the top of the tree, is dependent upon the hash of each transaction stored below in the tree. Each transaction 508 may include a set of data 510. The set of data 510 may include an identifier for the transaction (e.g., a unique string), and transaction data identifying the nature of the transaction and what the transactions entails.

In some embodiments, the blockchain 218 shown in FIG. 2B may be similar to the blockchain 502, and the transactions 116-126 shown in FIGS. 1B and 2B may be similar to the transaction 508. In some embodiments, the ledger 114 may share some of the functionality of the system 500, as well as the organization of blocks and transactions.

Smart Home Data

Figure 6A:
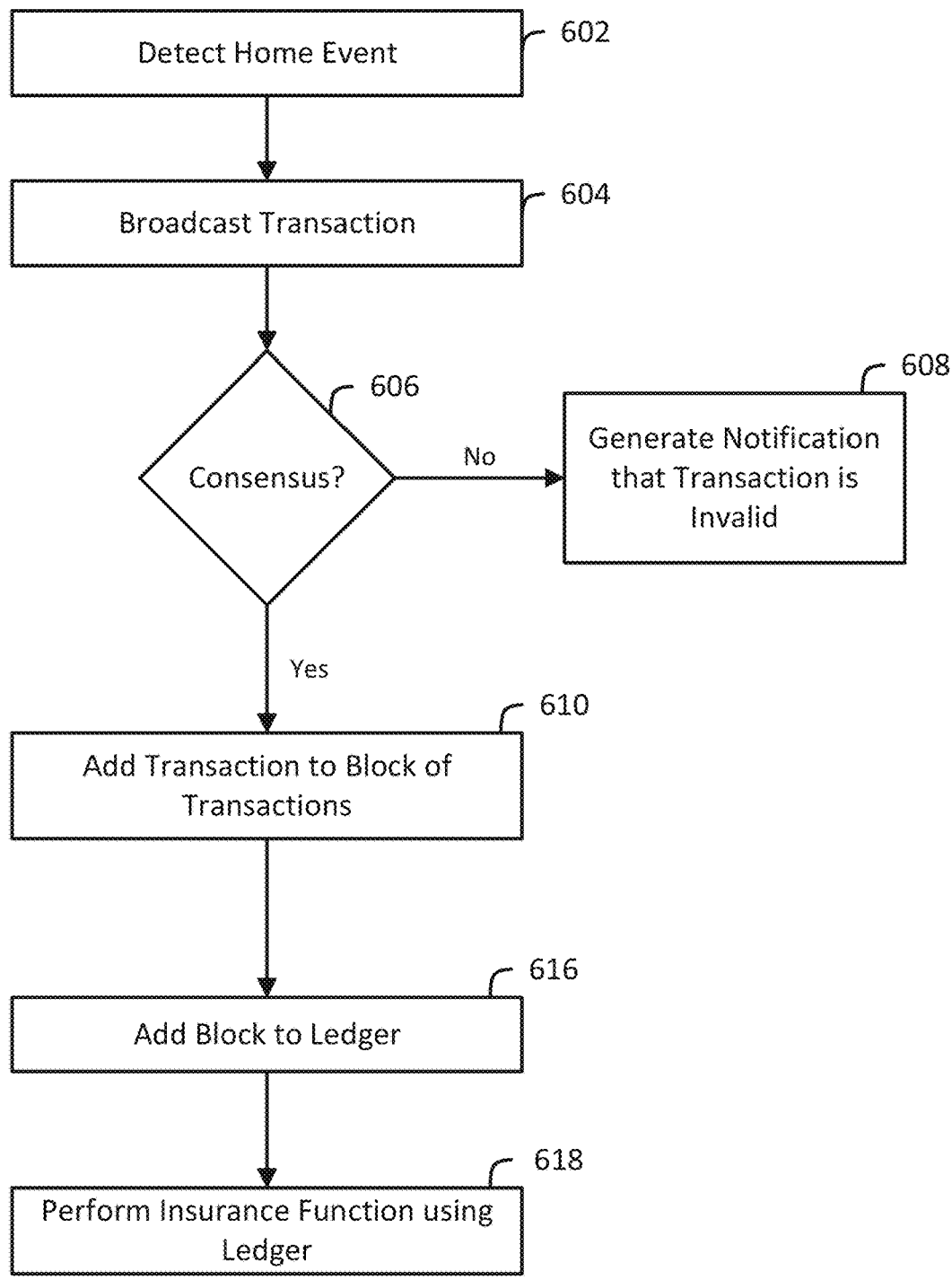
FIG. 6A depicts an exemplary computer-implemented method for tracking home events utilizing a distributed ledger in accordance with one aspect of the present disclosure.

In one embodiment, a distributed ledger is utilized to track smart home data. FIG. 6A depicts an exemplary computer-implemented method 600A of maintaining a distributed ledger (e.g., including a blockchain) on a home. The method 600A may include detecting (via one or more local or remote processors, sensors, servers, and/or transceivers) a home event (block 602).

A home event may be an insurance event (e.g., a new claim is filed; an estimate is generated; a claim is paid; etc.) and/or a smart home event detected by one or more home-based sensors and/or generated by one or more home-based computers. Detecting the home event may include receiving (e.g., at the node 102) notification of the insurance event or smart home event. The notification may include loss information, claim information, various sensor data, telematics data, intelligent home sensor or other data, mobile device data, and/or other data about insureds and insured assets, including that discussed elsewhere herein. For instance, the notification(s) may be received via wireless communication or data transmission over one or more radio frequency links or digital communication channels, and stored in a local memory.

Example smart home events include: motion detected by a motion detector; a door opening or closing detected by a door sensor; a window opening or closing detected by a window sensor; a temperature reading obtained by a thermostat; a desired temperature setpoint (e.g., entered by a person) detected by a thermostat; a carbon monoxide reading obtained by a carbon monoxide detector; a smoke reading detected by a smoke detector; a light status detected by a light sensor; a water flow detected by a flow sensor; a utility meter (e.g., gas, water, electric, etc.) reading obtained by a utility meter; etc.

The method 600A may include generating (via one or more local or remote processors, sensors, servers, and/or transceivers) a transaction and proposing the transaction (block 604). The transaction may be generated by the node 102, and the node 102 may broadcast the transaction to the nodes 104 and/or 106. The transaction may include data relating to the detected home event. For example, the transaction may include loss information, claim information, various sensor data, telematics data, intelligent home sensor or other data, mobile device data, and/or other data about the home, occupants in the home, the insured, etc.

The method 600A may include performing a consensus analysis (block 606). For example, the nodes 102, 104, and 106 may attempt to form a consensus, using any suitable consensus protocol (such as the hashing and problem solving technique previously described) as to whether the transaction is valid. In instances when consensus is not reached, the broadcasted transaction is not added to the ledger 114 and notification that the transaction is invalid may be generated (block 608).

The method 600A may include reaching consensus, adding the transaction to a block (block 610), and adding the block to a blockchain stored at the distributed ledger 114 if the block is not already part of the block chain (block 616). For example, the nodes 102-106 may reach consensus and may add the transaction to the distributed ledger 114 by each adding the transaction to a local copy of a block stored on a local copy of the distributed ledger 114.

The method 600A may include performing an insurance function using the distributed ledger 114 (block 618). For example, an insurance premium may be calculated based upon data (corresponding to one or more home events) stored at the ledger 114. As another example, damage to a home may be estimated based upon data stored at the ledger 114. To illustrate, one or more roof-based sensors and/or drone sensors may detect damage and write to the ledger 114 accordingly. As yet another example, an insured individual may access the ledger 114 to review: the status of various smart devices in a home, utility readings, security notifications, camera feeds, etc.

The nodes that implement the method 600A may be any one or more of the following: a server (e.g., of the insurance provider), a mobile device (e.g., a tablet, smart phone, or laptop of the insured or of a vendor), a desktop computer (e.g., of the insured or of a vendor), a smart device in a home (e.g., a smart thermostat, a smart carbon monoxide detector, a smart camera or microphone, or any other smart device), a home controller that manages other smart devices, a drone that surveys the home (e.g., for roof or siding damage), etc. Advantageously, after the blockchain has been updated, each of the nodes 102, 104, and 106 can access and review the transaction including the information relating to the home event.

Figure 6B:
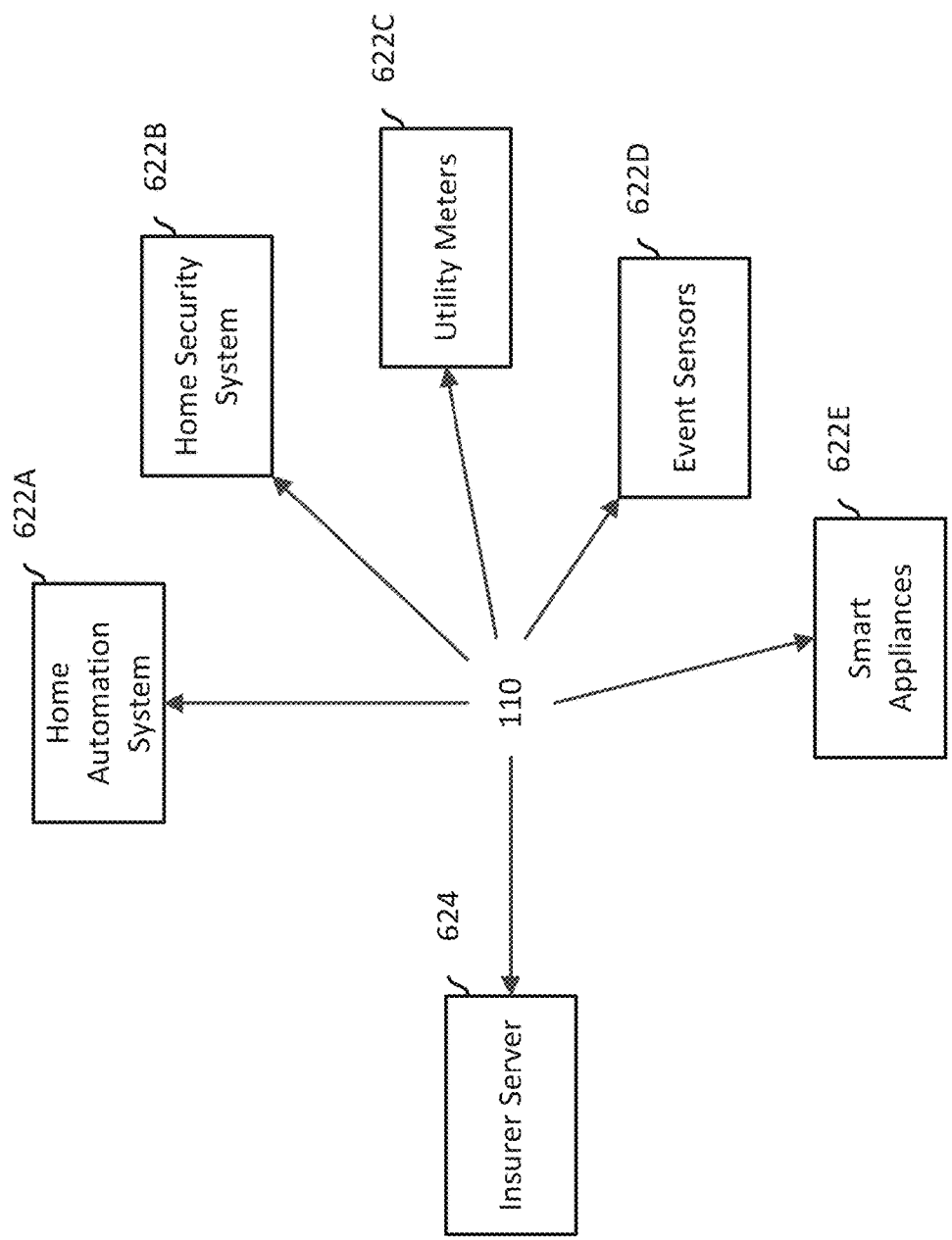
FIG. 6B is a block diagram of exemplary nodes that may utilize the distributed ledger discussed with reference to FIG. 6A, in accordance with one aspect of the present disclosure.

FIG. 6B is a block diagram of example nodes that may utilize the ledger 114 when implementing the method 600A. The example nodes may include in-home data sources 622A-622E and an insurer server 624, each of which may be connected to the others via communication links 110.

Each of the in-home data sources 622A-622E in FIG. 6B represents one or more devices at a building of an insurance policy holder. The home automation system data source 622A may be any suitable automation system for monitoring and controlling devices and appliances (e.g., doors, thermostats, lights, ovens, etc.) within a home. The home security system data source 622B may be any suitable security system, including, e.g., cameras, motion sensors, etc. The utility meters data source 120C may include utility meter devices, such as a water meter that includes a water volume sensor, a gas meter that includes a gas sensor, an electricity meter that includes an electricity sensor, etc. The "event sensors" data source 120D may include any of various other types of sensor devices, such as fire or smoke detectors, carbon monoxide detectors, thermostats, water detectors or flow meters (e.g., to detect a water leak), door/window sensors, glass break sensors, temperature sensors, humidity sensors, door lock sensors, energy monitors, etc. In certain embodiments, data from different sources may be combined to determine whether an event has occurred. For example, data indicating that a power outage has occurred may be combined data indicating large amounts of rainfall to indicate that consumers may face a higher chance that their sump pumps aren't working and their homes or businesses might be experiencing water loss.

The smart appliances data source 622E may include smart appliance devices that generate information relating to their usage, such as a smart refrigerator that indicates the temperature settings and how often the water filter is changed, a smart washing machine that generates repair/maintenance codes, or a smart light bulb, for example. Still other types of data sources, not shown in FIG. 6B, may also write or access the ledger 114. For example, a camera in the home of a policy holder may provide video data which may be processed in order to detect movement and/or other behaviors and/or conditions (e.g., detecting smoke in the field of view of the camera). Not all data sources need be located in the interior of a monitored property, or in a living quarters portion of a residential property. For example, a tilt sensor that indicates whether a garage door is open, and/or an outdoor movement sensor or camera mounted on an exterior wall of a home, may provide data to the ledger 114. Further, not all data sources need be permanent fixtures. For example, the event sensors data 622D may include a smartphone with global positioning system (GPS) sensors that generate location data, which may be utilized to determine whether the smartphone owner (e.g., the policy holder or a family member) is at home.

Smart Vehicle Data

Figure 7:
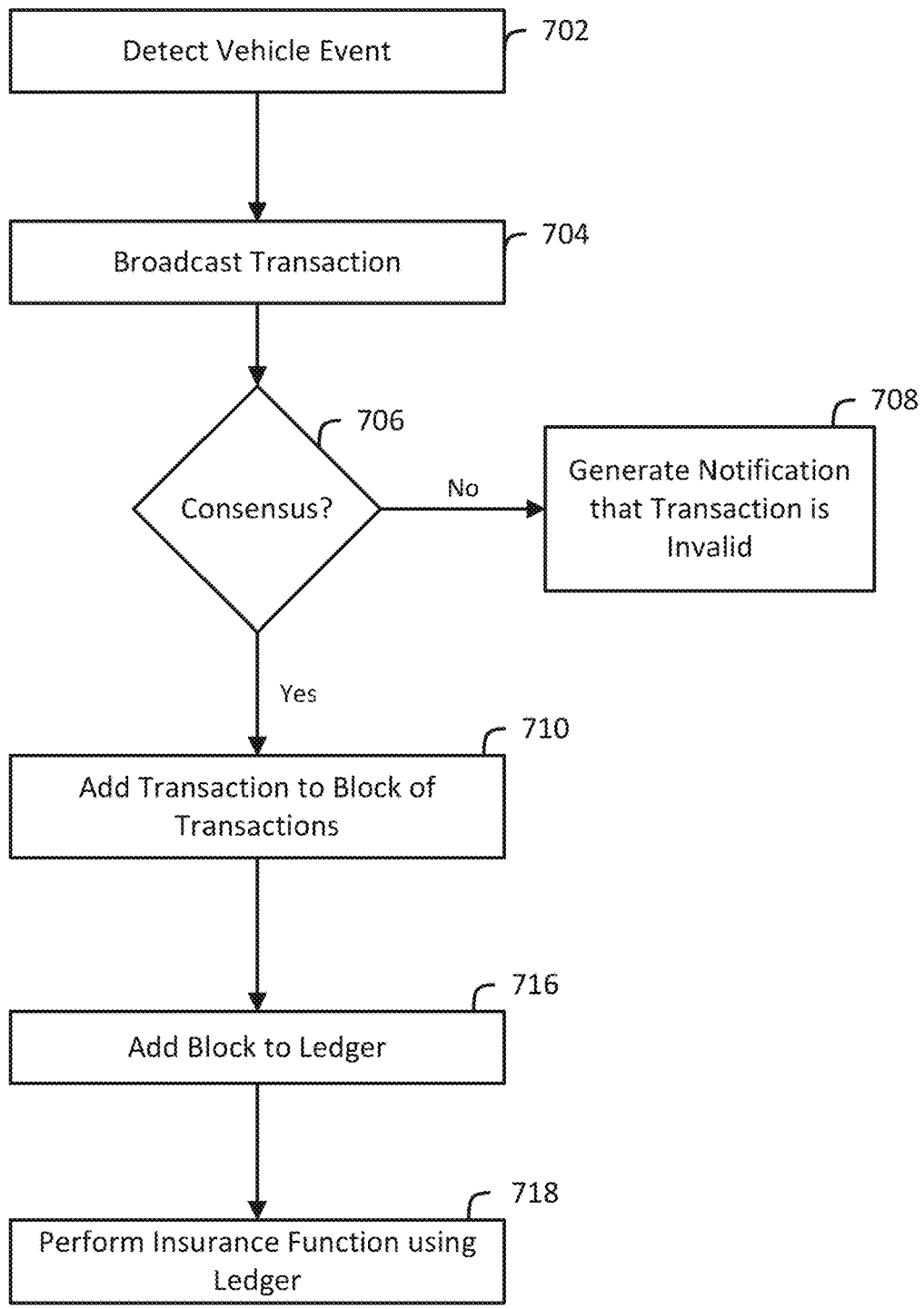
FIG. 7 depicts an exemplary computer-implemented method for tracking vehicle events utilizing a distributed ledger in accordance with one aspect of the present disclosure.

In one embodiment, a distributed ledger is utilized to track smart or autonomous vehicle data. FIG. 7 depicts an exemplary computer-implemented method 700 of maintaining a distributed ledger (e.g., including a blockchain) on a vehicle. The vehicle may be an autonomous vehicle, semi-autonomous vehicle, or a non-autonomous vehicle, depending on the embodiment. The method 700 may include detecting (via one or more local or remote processors, sensors, servers, and/or transceivers) a vehicle event (block 702).

A vehicle event may be an insurance event relating to a vehicle (e.g., a new claim is filed; an estimate is generated; a claim is paid; etc.) and/or a smart vehicle event detected by one or more vehicle-based sensors and/or generated by one or more vehicle-based computer systems. Detecting the vehicle event may include receiving (e.g., at the node 102) notification of the insurance event or smart vehicle event. The notification may include loss information, claim information, various sensor data, telematics data, intelligent vehicle sensor or other data, mobile device data, and/or other data about insureds and insured assets, including that discussed elsewhere herein. For instance, the notification(s) may be received via wireless communication or data transmission over one or more radio frequency links or digital communication channels, and stored in a local memory.

Example smart vehicle events include: a motion or position detected by a motion or position sensor as a GPS chip, an accelerometer, a compass, a speedometer, a gyroscope, etc.; braking detected by a braking sensor; turn input detected by a steering wheel sensor; wheel position detected by a wheel sensor; engine temperature detected by a temperature gauge; oil temperature detected by a temperature gauge; a seatbelt status detected by a seatbelt and/or seat sensor; a lane detection detected by a laser or radar based sensor; a proximate vehicle detected by a laser or radar based sensor; environmental conditions of a road detected by one or more cameras and/or laser systems; a door opening or closing detected by a door sensor; a window opening or closing detected by a window sensor; a temperature reading obtained by a temperature gauge; a desired temperature setpoint (e.g., entered by a person) detected via a temperature control system; etc.

The method 700 may include generating (via one or more local or remote processors, sensors, servers, and/or transceivers) a transaction and proposing the transaction (block 704). The transaction may be generated by the node 102, and the node 102 may broadcast the transaction to the nodes 104 and/or 106. The transaction may include data relating to the detected vehicle event. For example, the transaction may include loss information, claim information, various sensor data, telematics data, intelligent home sensor or other data, mobile device data, and/or other data about the vehicle, the driver, the insured, etc.

The method 700 may include performing a consensus analysis (block 706). For example, the nodes 102, 104, and 106 may attempt to form a consensus, using any suitable consensus protocol (such as the hashing and problem solving technique previously described) as to whether the transaction is valid. In instances when consensus is not reached, the broadcasted transaction is not added to the ledger 114 and notification that the transaction is invalid may be generated (block 708).

The method 700 may include reaching consensus, adding the transaction to a block (block 710), and adding the block to a blockchain stored at the distributed ledger 114 if the block is not already part of the block chain (block 716). For example, the nodes 102-106 may reach consensus and may add the transaction to the distributed ledger 114 by each adding the transaction to a local copy of a block stored on a local copy of the distributed ledger 114.

The method 700 may include performing an insurance function using the distributed ledger 114 (block 718). For example, an insurance premium may be calculated based upon data (corresponding to one or more home events) stored at the ledger 114. As another example, damage to a vehicle may be estimated based upon data stored at the ledger 114. As yet another example, an insured individual may access the ledger 114 to review: measurements from one or more location and/or position sensors in the vehicle; readings from one or more camera and/or laser systems for detecting proximate vehicles; one or more readings from a speedometer and/or trip meter; one or more parameters detected and/or generated by a vehicle-based computer; etc.

The nodes that implement the method 700 may be any one or more of the following: a server (e.g., of the insurance provider), a mobile device (e.g., a tablet, smart phone, or laptop of the insured or of a vendor), a desktop computer (e.g., of the insured or of a vendor), a smart sensor or device in a vehicle, an in-vehicle computer or "carputer," etc.

Insurance Claim Payouts

In one embodiment, a distributed ledger is utilized to track insurance claim payment activity. The present embodiments may be configured to track estimates, offers, settlements, and payouts relating to insurance claims relating to injuries, property damage, (e.g., to homes, automobile, personal articles, or other insured assets), and other expenses (e.g., payments to vendors such as car repair shops, car rental companies, cleaning companies, contractors, etc.).

Figure 8:
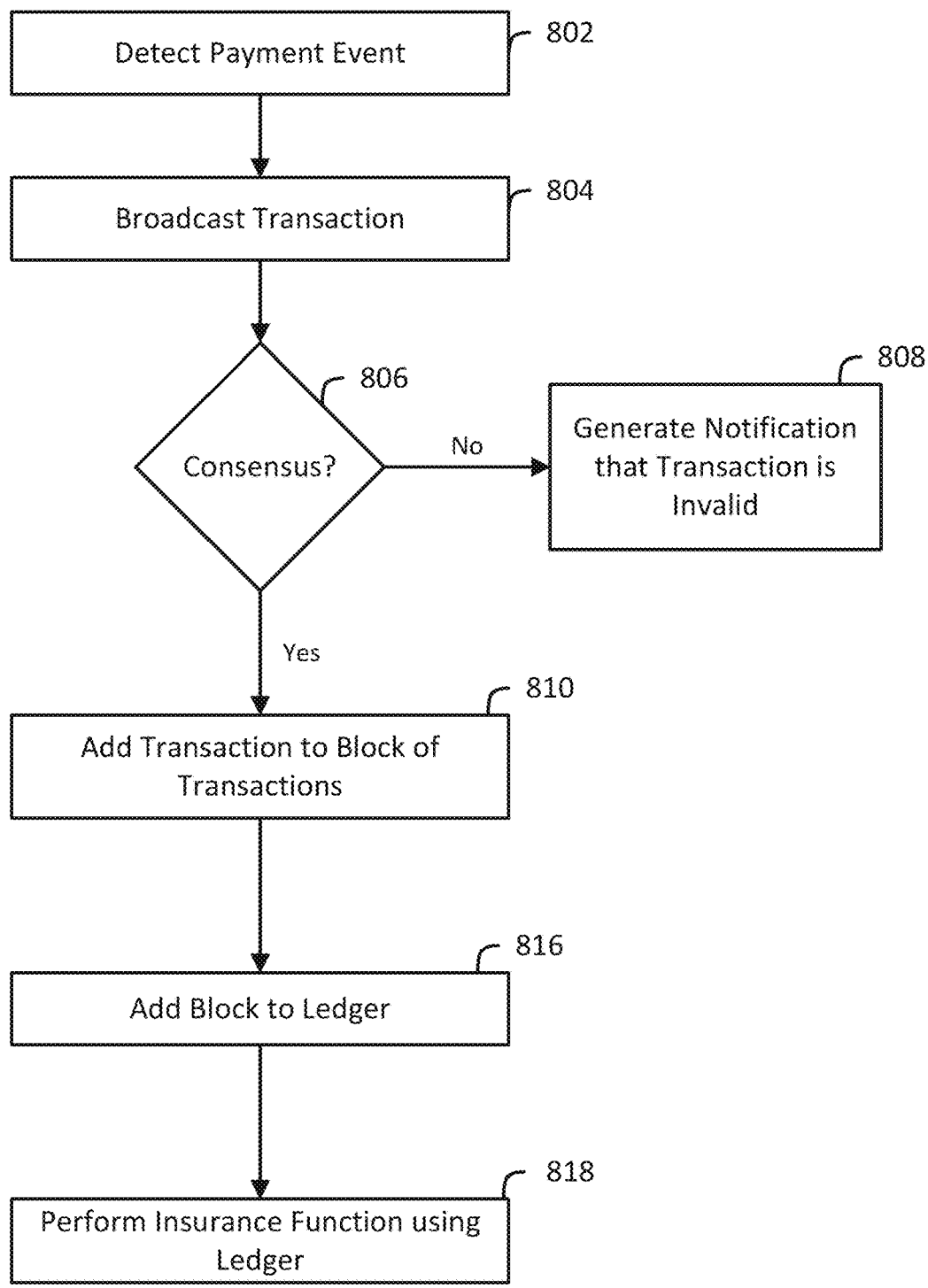
FIG. 8 depicts an exemplary computer-implemented method for tracking insurance claim payment activity utilizing a distributed ledger in accordance with one aspect of the present disclosure.

FIG. 8 depicts an example method 800 for managing, via a distributed ledger, insurance claim payment activity. The method 800 may be implemented, in whole or in part, by the system 112 shown in FIG. 1B. The method 800 may be saved to a memory as one or more instructions or routines.

The method 800 may include detecting (via one or more local or remote processors, sensors, servers, and/or transceivers) a payment event relating to an insurance claim (block 802). The payment event may be any one or more of: a calculation of an estimate, a submission of an offer, an arrival at a settlement, and/or an initiation and/or completion of a payment.

The estimate may be any one or more of: (i) an estimated cost to repair or replace damaged property (e.g., real estate such as a home, apartment, office building, industrial warehouse, etc; a vehicle; personal property such as jewelry, clothes, electronics, etc.); (ii) an estimated cost to compensate for special damages (e.g., medical bills, out-of-pocket expenses, and/or lost income); and/or (iii) an estimated cost for other expenses (e.g., payments to vendors such as car repair shops, car rental companies, cleaning companies, contractors, etc.).

The offer may be made by the insurer to the insured based upon the estimate. The offer may be the same as the estimate, or may be adjusted based upon a number of factors (e.g., a determination of fault). The settlement may be an agreement reached between the insured and insurer as to the value of a payout. Depending on the circumstances, the settlement amount may be less than, equal to, or more than the offer. The payment may be made by the insurer to the insured and/or to a vendor.

After the payment event is detected, the node 102 generates a transaction including data pertaining to the payment event and broadcasts the transaction (block 804). For example, when the payment event is a calculation of an estimate, the transaction may include data relating to one or more of the following: (1) an amount of the estimate; (2) an indication of whether the estimate relates to property damage, personal injuries, and/or other expenses; (3) a date on which the estimate was calculated; (4) an assessor who calculated the estimate; (5) a description of the damage the estimate is based upon; (6) an indication of whether property is to be repaired or replace; (7) an indication of any particular special damages the estimate is based upon, such as medical costs, out-of-pocket expenses, and/or lost income; and/or (8) one or more vendors to be compensated based upon the estimate (e.g., when the estimate relates to a rental car cost or a repair cost).

When the payment event is a submission of an offer, the transaction may include data relating to one or more of the following: (1) an offer amount; (2) a date on which the offer was made; and/or (3) a party (e.g., the insured) to whom the offer was made.

When the payment event is an arrival at a settlement, the transaction may include data relating to one or more of the following: (1) a settlement amount; (2) a date on which the settlement was made; (3) a party (e.g., the insured) with whom the settlement was made.

When the payment event is a payment, the transaction may include data relating to one or more of the following: (1) the amount of the payment; (2) the date and/or time the payment was initiated; (3) the date and/or time the payment was completed; (4) the recipient of the payment (e.g., the insured or a vendor); and/or (5) a payment status indicating that the payment has been made.

The method 800 may include performing a consensus analysis (block 806). For example, the nodes 102, 104, and 106 may attempt to form a consensus, using any suitable consensus protocol (such as the hashing and problem solving technique previously described) as to whether the transaction is valid. In instances when consensus is not reached, the broadcasted transaction is not added to the ledger 114 and notification that the transaction is invalid may be generated (block 808).

The method 800 may include reaching consensus, adding the transaction to a block (block 810), and adding the block to a blockchain stored at the distributed ledger 114 if the block is not already part of the block chain (block 816). For example, the nodes 102-106 may reach consensus and may add the transaction to the distributed ledger 114 by each adding the transaction to a local copy of a block stored on a local copy of the distributed ledger 114.

The method 800 may include performing an insurance function using the distributed ledger 114 (block 818). For example, an insured individual may file a claim; an insurance provider may assess damage and/or injury; the insurance provider may estimate a cost to repair or replace property and/or to treat an injury; the insurance provider may offer a claim payout; the insured individual may reject the offer and/or make a counter-offer; the insurance provider and the insured individual may reach a settlement; and/or the insurance provider may pay the claim.

The nodes that implement the method 800 may be any one or more of the following: a server (e.g., of the insurance provider), a mobile device (e.g., a tablet, smart phone, or laptop of the insured or of a vendor), a desktop computer (e.g., of the insured or of a vendor), etc. The nodes may read and/or write to the distributed ledger 114 for any of a number of reasons. For example, an insurer may: calculate one or estimates and store data pertaining to the one or more estimates to the ledger 114; provide one or more offers for property damage, special damages, and/or other expenses, and store data pertaining to the one or more offers to the ledger 114; arrive at a settlement and store data pertaining to the settlement to the ledger 114; and/or make a payment on the claim and store data pertaining to the payment to the ledger 114.

Further, an insured may access the ledger 114 to view the insurers estimate, offer, settlement, and/or payment status. Further, the insured may write to the ledger 114 to accept an offer, reject an offer, broadcast a counter offer, and/or reach a settlement with the insurer. Similarly, a vendor may write to the ledger 114 to accept an offer, reject an offer, broadcast a counter offer, and/or accept a payment for services rendered (e.g., car repair, car rental, home repair, etc.).

Insurance Carrier Discovery

In one embodiment, a distributed ledger is utilized for insurance carrier discovery. The present embodiments may be configured to track insured individuals, their insurance policies, the insurance companies holding each of their policies, etc. Such embodiments may be useful, for example, for facilitating exchange of insurance information between drivers after an automobile accident when drivers want to exchange insurance information and/or verify that the other is insured, facilitating subrogation (e.g., when an insurance company pays for an first insured party's losses but subsequently pursues reimbursement from an insurance company of a second at-fault party), and/or facilitating a determination of whether a driver has excess liability coverage.

Figure 9:
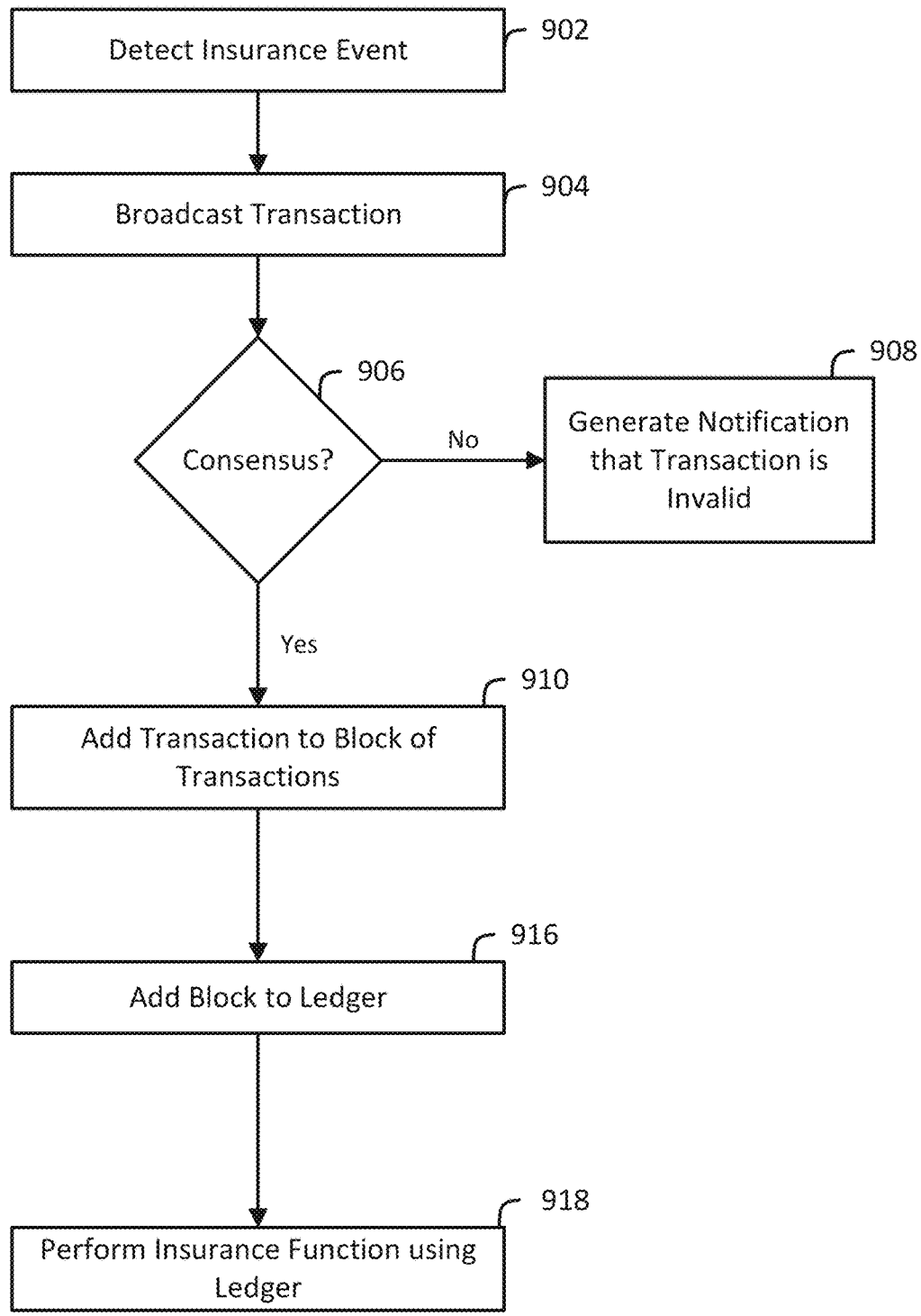
FIG. 9 depicts an exemplary computer-implemented method for managing, via a distributed ledger, insurance information in accordance with one aspect of the present disclosure.

FIG. 9 depicts an example method 900 for managing, via a distributed ledger, insurance information. The method 900 may be implemented, in whole or in part, by the system 112 shown in FIG. 1B. The method 900 may be saved to a memory as one or more instructions or routines.

The method 900 may include detecting (via one or more local or remote processors, sensors, servers, and/or transceivers) an insurance event (block 902). The insurance event may be any one or more of: an insured acquiring an insurance policy; the insured updating the insurance policy; the insured filing a claim; etc.

The method 900 may include generating (e.g., by the node 102) a transaction including data pertaining to the insurance event and proposing the transaction (block 904). The data may include: an identifier for the insured (e.g., a SSN and/or name); an identifier for each policy held by the insured; a description of each policy held by the insured; limits and premiums for each policy held by the insured; an insurance provider that provides each policy held by the insured; etc.

The method 900 may include performing a consensus analysis (block 906). For example, the nodes 102, 104, and 106 may attempt to form a consensus, using any suitable consensus protocol (such as the hashing and problem solving technique previously described) as to whether the transaction is valid. In instances when consensus is not reached, the broadcasted transaction is not added to the ledger 114 and notification that the transaction is invalid may be generated (block 808).

The method 900 may include reaching consensus, adding the transaction to a block (block 910), and adding the block to a blockchain stored at the distributed ledger 114 if the block is not already part of the block chain (block 816). For example, the nodes 102-106 may reach consensus and may add the transaction to the distributed ledger 114 by each adding the transaction to a local copy of a block stored on a local copy of the distributed ledger 114.

The method 900 may include performing an insurance function using the distributed ledger 114 (block 918). For example, insured individuals may exchange insurance information after an automobile accident; a third party (e.g., a policeman) may verify that a driver has insurance; an insurance provider may subrogate a claim; an insurance provider and/or third party may make a determination as to whether an individual has excess liability coverage; etc.

For example, an insurance premium may be calculated based upon data (corresponding to one or more home events) stored at the ledger 114. As another example, damage to a vehicle may be estimated based upon data stored at the ledger 114. As yet another example, an insured individual may access the ledger 114 to review: measurements from one or more location and/or position sensors in the vehicle; readings from one or more camera and/or laser systems for detecting proximate vehicles; one or more readings from a speedometer and/or trip meter; one or more parameters detected and/or generated by a vehicle-based computer; etc.

The nodes that implement the method 900 may be any one or more of the following: a server (e.g., of the insurance provider), a mobile device (e.g., a tablet, smart phone, or laptop of the insured or of a vendor), a desktop computer (e.g., of the insured or of a vendor), etc. The nodes may read and/or write to the distributed ledger 114 for any of a number of reasons. For example, an insurer may update the ledger 114 any time a new policy is generated or any time a policy is updated. As another example, an insured may access the ledger 114 to check his or her policies, carriers, limits, premiums, deductibles, etc. Similarly, a third party may access the ledger 114 to check an insureds policies, carriers, limits, etc. The ledger 114 may be particularly useful after an accident, when drivers want to exchange insurance information or when someone wants to verify an insurance carrier of an insured individual.

ADDITIONAL CONSIDERATIONS

With the foregoing, an insurance customer may opt-in to a rewards, insurance discount, or other type of program (such as a UBI program). After the insurance customer provides their affirmative consent, an insurance provider remote server may collect data from the customer's mobile device, smart vehicle, autonomous vehicle, smart home controller, or other smart devices. The data collected may be related to smart or autonomous vehicle functionality, smart home functionality (or home occupant preferences or preference profiles), and/or insured assets before (and/or after) an insurance-related event, including those events discussed elsewhere herein. In return, risk averse insureds, home or vehicle owners, or home, vehicle, or apartment occupants may receive discounts or insurance cost savings related to home, renters, personal articles, auto, and other types of insurance from the insurance provider.

In one aspect, telematics data, smart or autonomous vehicle data, mobile device data, smart or interconnected home data, and/or other data, including the types of data discussed elsewhere herein, may be collected or received by an insurance provider remote server (e.g., via direct or indirect wireless communication or data transmission from a smart home controller, mobile device, or other customer computing device) after a customer affirmatively consents or otherwise opts-in to an insurance discount, reward, or other program. The insurance provider may then analyze the data received with the customer's permission to provide benefits to the customer. As a result, risk averse customers may receive insurance discounts or other insurance cost savings based upon data that reflects low risk behavior and/or technology that mitigates or prevents risk to (i) insured assets, such as homes, personal belongings, or vehicles, and/or (ii) individuals.

This detailed description is to be construed as exemplary only and does not describe every possible embodiment, as describing every possible embodiment would be impractical, if not impossible. One may be implement numerous alternate embodiments, using either current technology or technology developed after the filing date of this application.

Further to this point, although the embodiments described herein often utilize credit report information as an example of sensitive information, the embodiments described herein are not limited to such examples. Instead, the embodiments described herein may be implemented in any suitable environment in which it is desirable to identify and control specific type of information. As part of implementing the automotive claims process, vehicle loss history, and the lifecycle of a vehicle identification number, a financial institution may be a part of the process. For example, the aforementioned embodiments may be implemented by the financial institution to identify and contain bank account statements, brokerage account statements, tax documents, etc. To provide another example, the aforementioned embodiments may be implemented by a lender to not only identify, re-route, and quarantine credit report information, but to apply similar techniques to prevent the dissemination of loan application documents that are preferably delivered to a client for signature in accordance with a more secure means (e.g., via a secure login to a web server) than via email.

With the foregoing, a user may be an insurance customer who may opt-in to a rewards, insurance discount, or other type of program. After the insurance customer provides their affirmative consent, an insurance provider remote server may collect data from the customer's mobile device, smart home controller, smart vehicle, autonomous vehicle, or other smart devices—such as with the customer's permission or affirmative consent. The data collected may be related to smart or autonomous vehicle functionality, or smart home functionality (or home occupant preferences or preference profiles), and/or insured assets before (and/or after) an insurance-related event, including those events discussed elsewhere herein. In return, risk averse insureds, home owners, or drivers may receive discounts or insurance cost savings related to home, renters, personal articles, auto, and other types of insurance from the insurance provider.

Furthermore, although the present disclosure sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims. Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In exemplary embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

The patent claims at the end of this patent application are not intended to be construed under 35 U.S.C. § 112(f) unless traditional means-plus-function language is expressly recited, such as "means for" or "step for" language being explicitly recited in the claim(s).

What is claimed:

1. A computer-implemented method for tracking changes to statuses of insurance policies or claims pertaining to vehicles, the method comprising:
    implementing a plurality of servers, each of the plurality of servers maintaining a copy of a distributed ledger;
    detecting a change in a status of an existing insurance policy or claim pertaining to a vehicle;
    responding to the detection of the change in the status of the existing insurance policy or claim pertaining to the vehicle, including:
    (i) generating, via a first server from the plurality of servers, a transaction record for the distributed ledger including data corresponding to the change in the status;
    (ii) generating a hash value representative of at least the transaction record using at least a generated nonce value; and
    (iii) storing the transaction record and the hash value to each copy of the distributed ledger at the plurality of servers; and
    performing an insurance function based upon the transaction record stored to the distributed ledger.

2. The method of claim 1, wherein the change in the status represents any one or more of: a generation of a new insurance policy pertaining to the vehicle; a filing of a claim pertaining to the vehicle; an assessment of damage to the vehicle; an estimate of a repair or replacement cost for the vehicle; and a payment to settle the claim.

3. The method of claim 1, wherein responding to the detection further includes:
    performing, via the plurality of servers, a consensus analysis via a consensus mechanism to form a consensus regarding the validity of the transaction record, wherein storing the transaction record includes storing the transaction record in response to detecting that the consensus has been formed.

4. The method of claim 3, wherein the consensus mechanism is any one or more of: a proof of activity mechanism, a proof of burn mechanism, a proof of capacity mechanism, or a proof of elapsed time mechanism.

5. The method of claim 1, wherein the insurance function is a calculation of a premium.

6. The method of claim 1, wherein the insurance function is an assessment of damage or an estimate of a repair or replacement cost.

7. The method of claim 1, wherein the data corresponding to the change in the status includes any one or more of the following: an identifier for the active insurance policy covering the vehicle; a description of the active insurance policy; an identifier for an individual holding the active insurance policy; an identifier for an insurance provider providing the active insurance policy; a record of one or more claims filed under the active insurance policy; one or more limits and/or premiums for the active insurance policy; a detected speed of the vehicle; a detected acceleration of the vehicle; a detected position of the vehicle; a detected track of the vehicle; a detected braking by the vehicle; a detected turning of the vehicle; a detected proximate vehicle; a detected lane; a detected environmental condition; a detected road condition; and a detected ambient temperature.

8. The method of claim 1, wherein the data corresponding to the change in the status includes any one or more of the following: a detected opening or closing of a door of the vehicle; a measured engine temperature; a measured oil temperature; a measured cabin temperature; a seatbelt status; a detected weight on a seat; an image or video of the environment surrounding the vehicle; and an image or video of a cabin of the vehicle.

9. The method of claim 1, wherein storing the transaction record at the distributed ledger comprises: storing the transaction to a block.

10. The method of claim 9, wherein the hash value is a hash value for the block, and further wherein generating the hash value for the block includes generating a transaction hash value for the transaction and utilizing the transaction hash value for the transaction to generate the hash value for the block.

11. The method of claim 3, wherein the consensus mechanism is: the proof of work mechanism, the proof of stake mechanism, or the proof of activity mechanism.

12. The method of claim 3, wherein the consensus mechanism is: the proof of burn mechanism, the proof of capacity mechanism, or the proof of elapsed time mechanism.

13. A system for tracking changes to statuses of insurance policies or claims pertaining to vehicles, the system comprising:
 a plurality of servers, each including one or more processors and maintaining a copy of a distributed ledger for tracking changes in statuses of insurance policies or claims pertaining to vehicles, wherein the plurality of servers includes a first server and one or more other servers;
 wherein the first server is configured to respond to a detection of a change in a status of an existing insurance policy or claim pertaining to a vehicle by generating a transaction record for the distributed ledger including data corresponding to the change in the status; and
 wherein the plurality of servers are configured to: (i) generate a hash value representative of at least the transaction record using at least a generated nonce value; (ii) store the transaction record generated by the first server and the hash value to each copy of the distributed ledger at the plurality of servers; and (iii) perform an insurance function based upon the transaction record stored to the distributed ledger.

14. The system of claim 13, wherein the change in the status represents any one or more of: a generation of a new insurance policy pertaining to the vehicle; a filing of a claim pertaining to the vehicle; an assessment of damage to the vehicle; an estimate of a repair or replacement cost for the vehicle; and a payment to settle the claim.

15. The system of claim 13, wherein the first server is configured to broadcast the transaction record to the one or more other servers;
 wherein the plurality of servers are configured to: perform a consensus analysis via a consensus mechanism to form a consensus regarding the validity of the transaction record; and
 store the transaction record in response to detecting that the consensus has been formed.

16. The system of claim 15, wherein the consensus mechanism is any one or more of: a proof of activity mechanism, a proof of burn mechanism, a proof of capacity mechanism, or a proof of elapsed time mechanism.

17. The system of claim 13, wherein the insurance function is a calculation of a premium.

18. The system of claim 13, wherein the insurance function is an assessment of damage or an estimate of a repair or replacement cost.

19. The system of claim 13, wherein the data corresponding to the change in the status includes any one or more of the following: an identifier for the active insurance policy covering the vehicle; a description of the active insurance policy; an identifier for an individual holding the active insurance policy; an identifier for an insurance provider providing the active insurance policy; a record of one or more claims filed under the active insurance policy; one or more limits and/or premiums for the active insurance policy.

20. The system of claim 13, wherein the data corresponding to the change in the status includes any one or more of the following: a detected speed of the vehicle; a detected acceleration of the vehicle; a detected position of the vehicle; a detected track of the vehicle; a detected braking by the vehicle; a detected turning of the vehicle; a detected proximate vehicle; a detected lane; a detected environmental condition; a detected road condition; a detected ambient temperature; a detected opening or closing of a door of the vehicle; a measured engine temperature; a measured oil temperature; a measured cabin temperature; a seatbelt status; a detected weight on a seat; an image or video of the environment surrounding the vehicle; and an image or video of a cabin of the vehicle.

\* \* \* \* \*